US011974716B2

(12) United States Patent
Gocho et al.

(10) Patent No.: US 11,974,716 B2
(45) Date of Patent: May 7, 2024

(54) OPERATION SUPPORTING DEVICE AND METHOD OF OPERATING OPERATION SUPPORTING DEVICE

(71) Applicant: OLYMPUS CORPORATION, Hachioji (JP)

(72) Inventors: Tomoko Gocho, Hino (JP); Satoru Kikuchi, Hachioji (JP); Kosuke Kishi, Mitaka (JP); Takami Shibazaki, Sagamihara (JP); Hiromu Ikeda, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 1001 days.

(21) Appl. No.: 16/899,068

(22) Filed: Jun. 11, 2020

(65) Prior Publication Data
US 2020/0297422 A1 Sep. 24, 2020

Related U.S. Application Data

(63) Continuation of application No. PCT/JP2018/004038, filed on Feb. 6, 2018.
(Continued)

(51) Int. Cl.
*A61B 1/00* (2006.01)
*A61B 34/10* (2016.01)
*G06T 7/73* (2017.01)

(52) U.S. Cl.
CPC .... *A61B 1/00006* (2013.01); *A61B 1/000094* (2022.02); *A61B 1/000096* (2022.02);
(Continued)

(58) Field of Classification Search
CPC .......... A61B 1/00006; A61B 1/000094; A61B 1/000096; A61B 1/00045; A61B 1/00055;
(Continued)

(56) References Cited

U.S. PATENT DOCUMENTS 8,672,836 B2 * 3/2014 Higgins ........... A61B 1/000094
600/117
11,241,294 B2 * 2/2022 Tripathi ................. A61B 90/37
(Continued)

FOREIGN PATENT DOCUMENTS

CN 107887018 B * 9/2021
EP 2583619 B1 * 3/2022 ........... A61B 3/0025
(Continued)

OTHER PUBLICATIONS

Mar. 27, 2018 International Search Report issued in International Patent Application No. PCT/JP2018/004038.
(Continued)

*Primary Examiner* — Khai M Nguyen
(74) *Attorney, Agent, or Firm* — Oliff PLC

(57) ABSTRACT

A processor of an operation supporting device acquires pre-operation data including position information of a feature portion of an inside of a body cavity of a subject, which is generated before an operation, and a procedure in the operation, which is planned before the operation, and acquires an endoscope image generated in the operation. The processor generates real-time data including real-time position information of the feature portion of the inside of the body cavity, based at least on the pre-operation data and the endoscope image, and generates an image to be displayed on the endoscope image in a superimposed manner, based on the real-time data. The processor recognizes a real-time scene based at least on the procedure planned before the operation and the real-time data.

20 Claims, 15 Drawing Sheets

Related U.S. Application Data

(60) Provisional application No. 62/598,913, filed on Dec. 14, 2017.

(52) U.S. Cl.
CPC ...... *A61B 1/00045* (2013.01); *A61B 1/00055* (2013.01); *A61B 1/00147* (2013.01); *A61B 34/10* (2016.02); *G06T 7/73* (2017.01); *A61B 2034/107* (2016.02); *G06T 2207/10068* (2013.01)

(58) Field of Classification Search
CPC ................ A61B 1/00147; A61B 34/10; A61B 2034/107; G06T 7/73; G06T 2207/10068
See application file for complete search history.

(56) References Cited

U.S. PATENT DOCUMENTS

| | | |
|---|---|---|
| 2018/0220873 A1 | 8/2018 | Tani |
| 2018/0310809 A1 | 11/2018 | Watanabe et al. |
| 2019/0053857 A1 | 2/2019 | Sugie et al. |
| 2023/0111368 A1* | 4/2023 | Hu ..................... A61F 2/4657 606/102 |

FOREIGN PATENT DOCUMENTS

| | | | |
|---|---|---|---|
| JP | H05-337118 | A | 12/1993 |
| JP | H08-336497 | A | 12/1996 |
| JP | H10-80396 | A | 3/1998 |
| JP | 2004-199004 | A | 7/2004 |
| JP | 2007-07041 | A | 1/2007 |
| JP | 2009-56238 | A | 3/2009 |
| JP | 2009056238 | A * | 3/2009 |
| JP | 2014135974 | A * | 7/2014 |
| WO | 2017/061495 | A1 | 4/2017 |
| WO | 2017/110459 | A1 | 6/2017 |
| WO | 2017/145475 | A1 | 8/2017 |
| WO | 2017/160792 | A1 | 9/2017 |

OTHER PUBLICATIONS

Jun. 16, 2020 IPRP and Written Opinion issued International Patent Application No. in PCT/JP2018/004037.
Mar. 13, 2018 International Search Report issued in International Patent Application No. PCT/JP2018/004037.
Jun. 16, 2020 IPRP and Written Opinion issued International Patent Application No. in PCT/JP2018/004038.

* cited by examiner

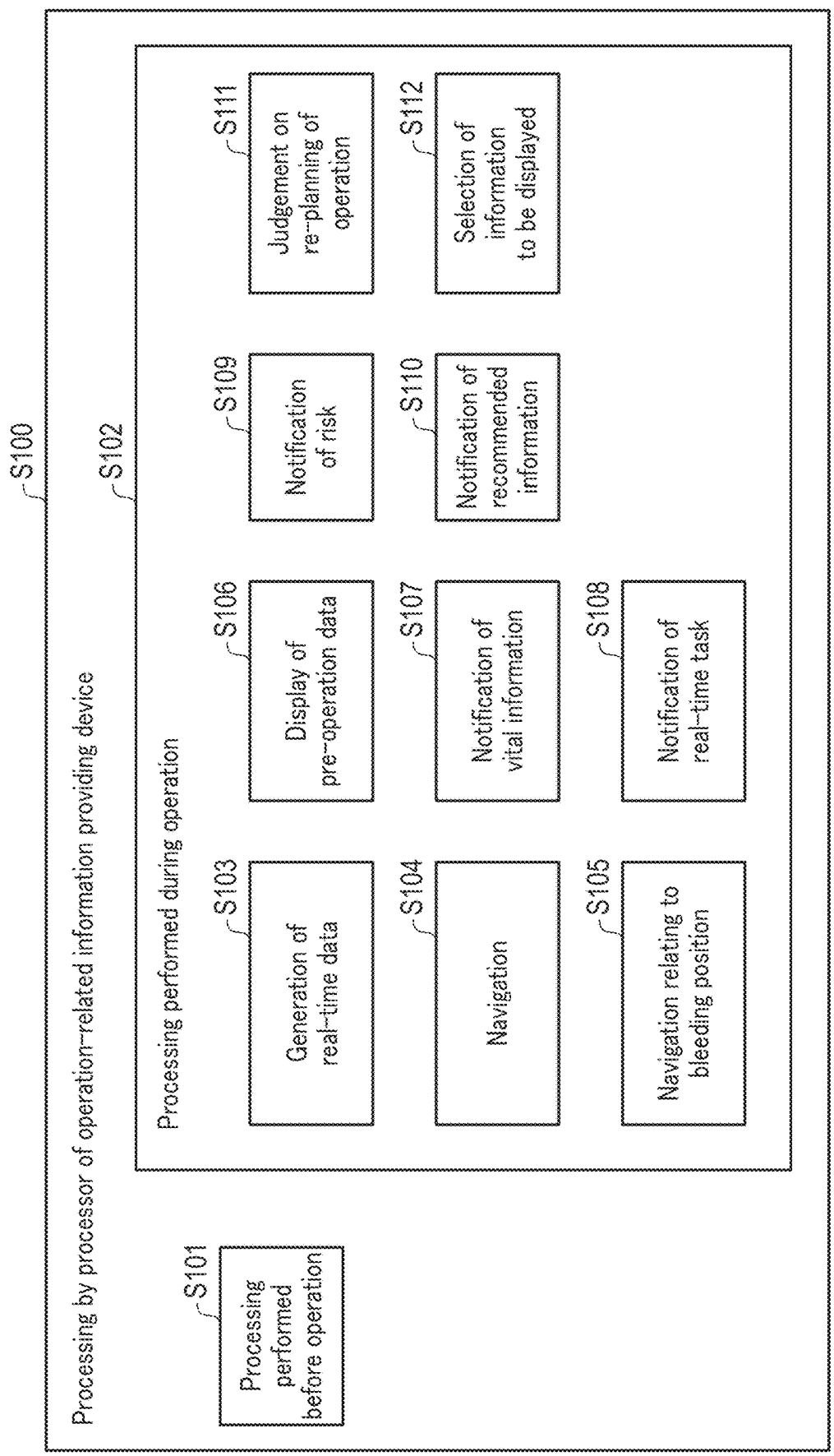
F I G. 2

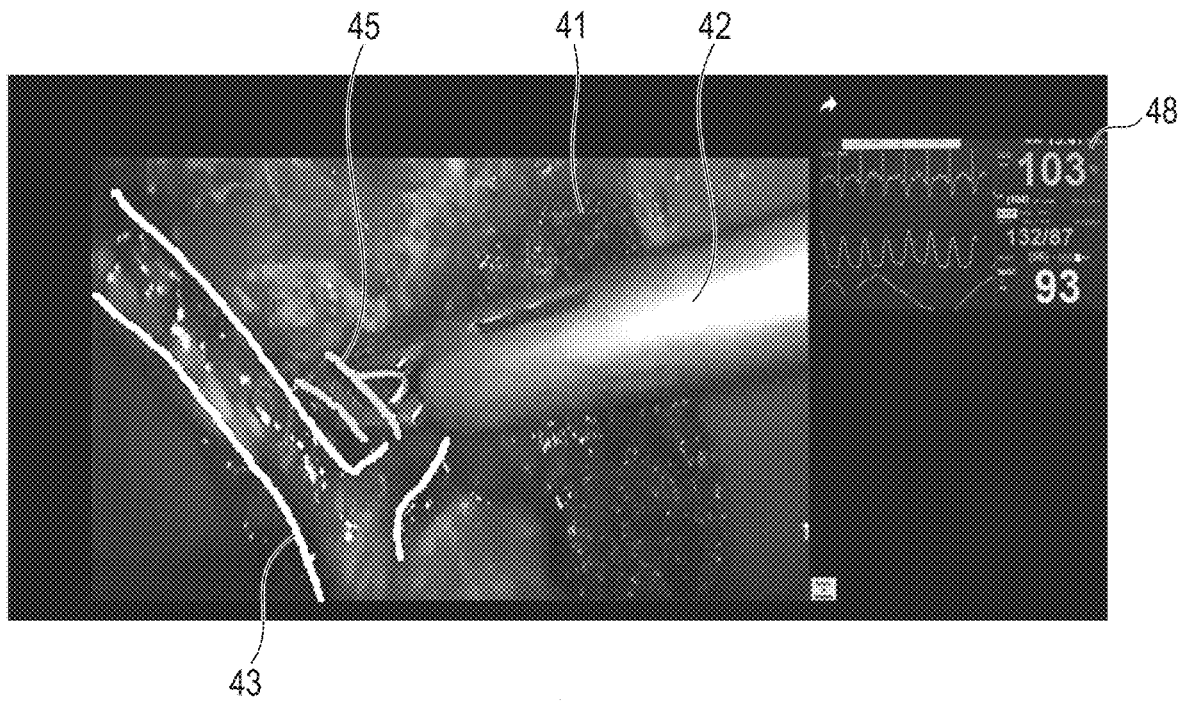
F I G. 11
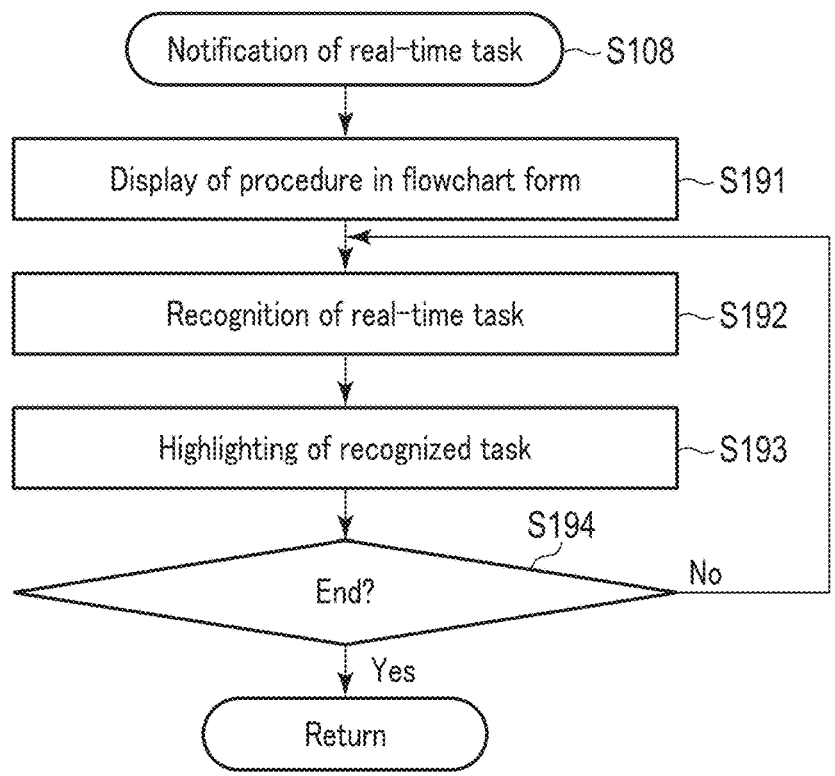
F I G. 12

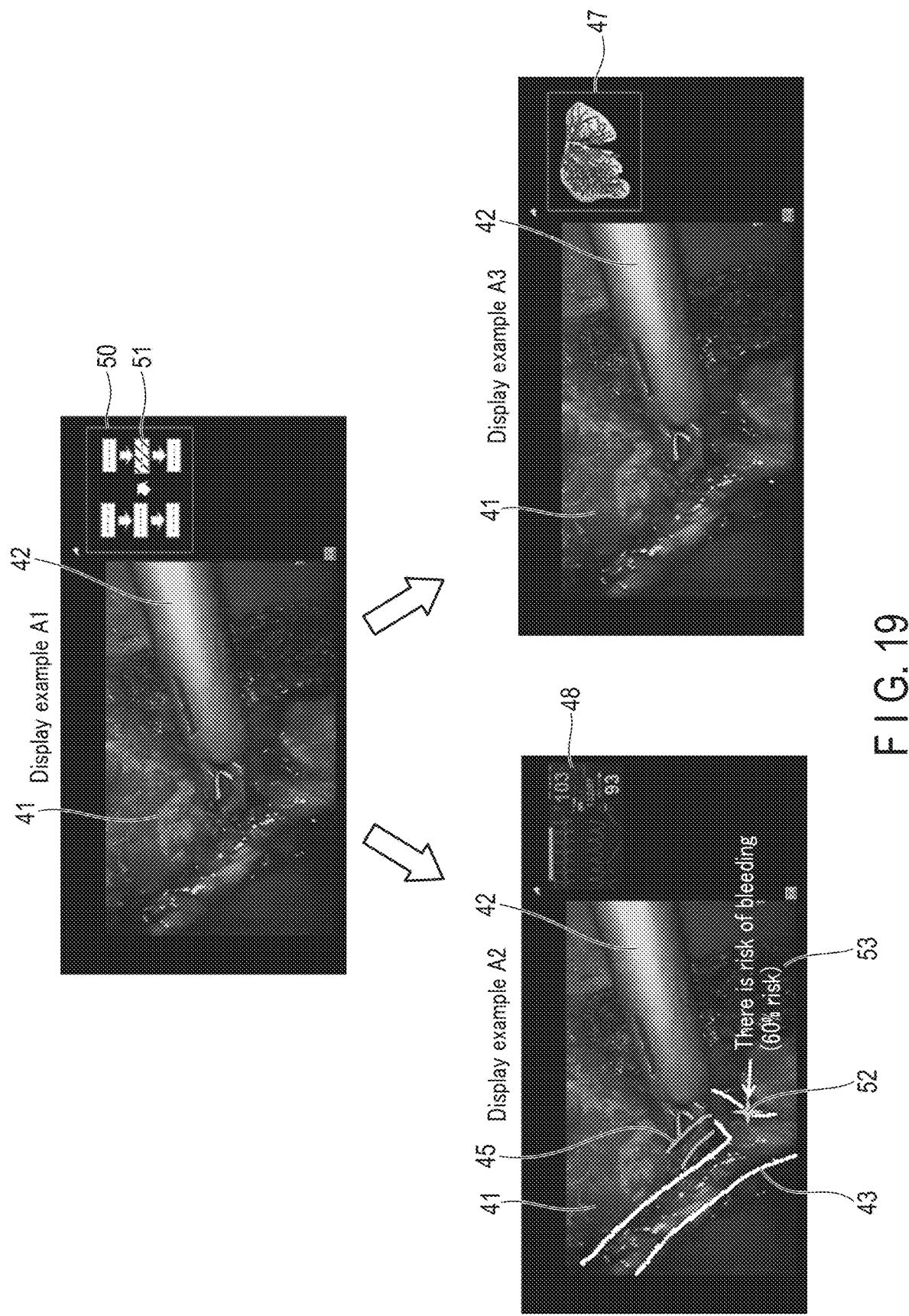

OPERATION SUPPORTING DEVICE AND METHOD OF OPERATING OPERATION SUPPORTING DEVICE

CROSS-REFERENCE TO RELATED APPLICATIONS

This is a Continuation Application of PCT Application No. PCT/JP2018/004038, filed Feb. 6, 2018 and based upon and claiming the benefit of priority from prior U.S. Provisional Application No. 62/598,913, filed Dec. 14, 2017, the entire contents of which are incorporated herein by reference.

BACKGROUND

Jpn. Pat. Appln. KOKAI Publication No. 2007-7041 discloses an operation supporting device for supporting an operator or the like in an operation. This operation supporting device generates 3D volume data of a subject from an image imaged by, for example, an MRI device before an operation, and extracts an image of a specific site from the 3D volume data. In the operation, the operation supporting device determines a projection plane to project the image of the specific site extracted from the 3D volume data, based on the position of an endoscope. The operation supporting device then generates a projection image of the specific site on the determined projection plane, and causes the generated projection image of the specific site to be displayed on an endoscope image in a superimposed manner.

BRIEF SUMMARY

Exemplary embodiments relate generally to an operation supporting device and a method of operating the operation supporting device.

An operation supporting device can include a processor configured to: acquire pre-operation data including position information of a tissue of an inside of a body cavity of a subject, which is generated before an operation, and a procedure in the operation, which is planned before the operation, and acquire an endoscope image generated in the operation; generate real-time data including real-time position information of the tissue of the inside of the body cavity, based at least on the pre-operation data and the endoscope image; generate an image to be displayed on the endoscope image in a superimposed manner, based on the real-time data; and recognize a real-time scene based at least on the procedure planned before the operation and the real-time data.

A method of operating an operation supporting device can include: acquiring an operation plan based on simulation, which is generated before an operation; acquiring an endoscope image generated in the operation; recognizing a tissue on the acquired endoscope image; generating real-time 3D volume data of an inside of a body cavity of a subject including the tissue, based at least on the acquired endoscope image; and recognizing a real-time scene based at least on the real-time 3D volume data and the operation plan.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 2 is a schematic diagram showing processing performed by a processor of the operation-related information providing device according to an exemplary embodiment.

FIG. 11 is a diagram showing an example of the state where the vital information is displayed together with the endoscope image in an exemplary embodiment.

FIG. 12 is a flowchart showing processing performed in notification of a real-time task by the processor of the operation-related information providing device according to an exemplary embodiment.

FIG. 19 is a diagram illustrating selection of information to be displayed, which is performed by the processor of the operation-related information providing device according to an exemplary embodiment.

DETAILED DESCRIPTION

Figure 1:
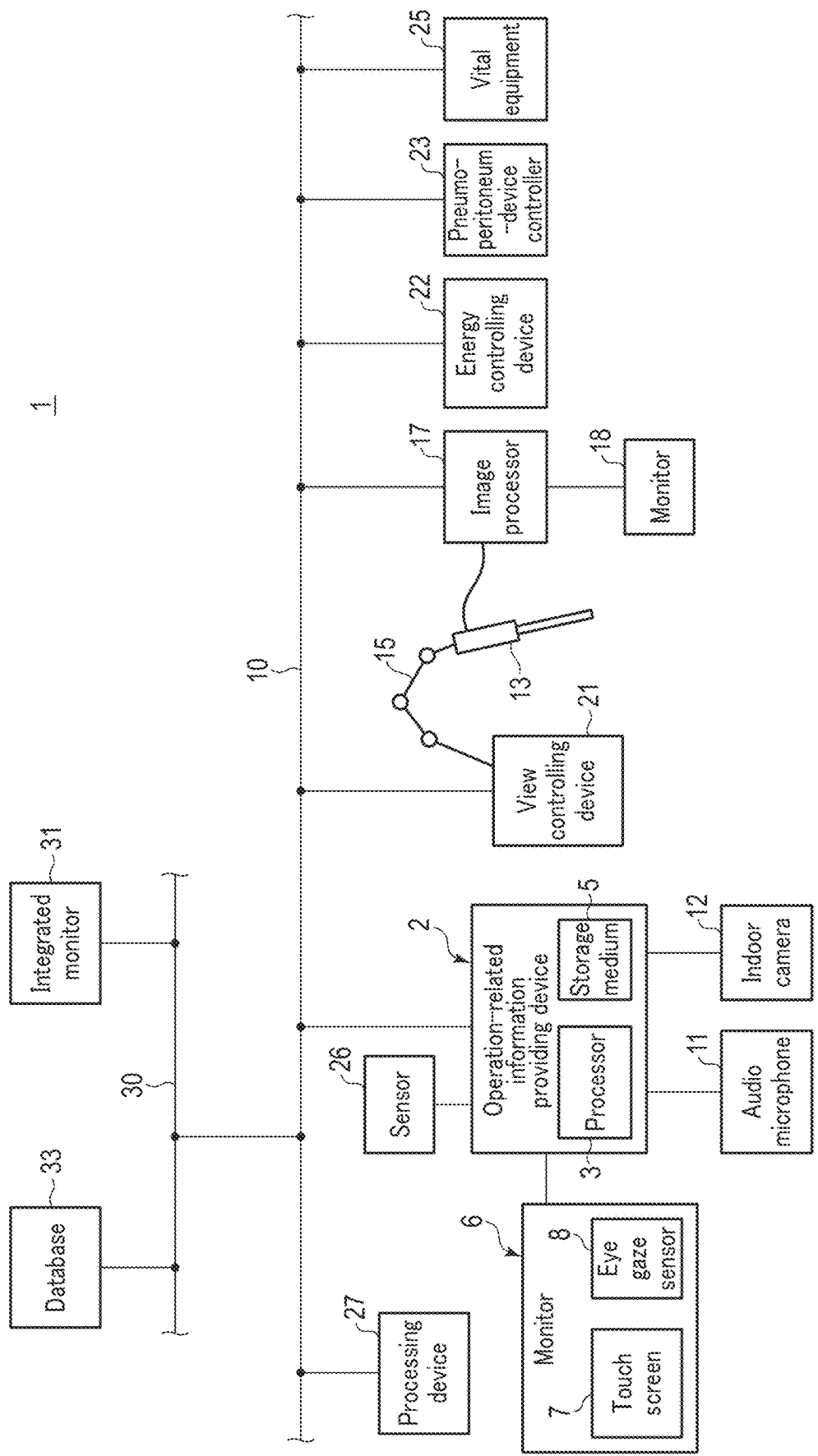
FIG. 1 is a schematic diagram showing a system including an operation-related information providing device according to an exemplary embodiment.

An exemplary embodiment will be described with reference to FIGS. 1 to 19. FIG. 1 shows a system 1 including an operation-related information providing device 2, which is an operation supporting device of the present embodiment. As shown in FIG. 1, the operation-related information providing device 2 of the system 1 includes a processor 3 and a storage medium 5. The processor 3 is formed of an integrated circuit or the like including a central processing unit (CPU), an application specific integrated circuit (ASIC), a field programmable gate array (FPGA), or the like. The operation-related information providing device 2 may include only one processor 3 or a plurality of processors 3. Processing in the processor 3 is performed in accordance with a program stored in the processor 3 or a storage medium 5. The storage medium 5 stores a processing program used by the processor 3 and a parameter, function, table, and the like used in a computation by the processor 3. In an example, the processor 3 implements processing to be described later through learning using artificial intelligence (AI). The processor 3 provides operation-related information, as will be described below.

In the system 1, the operation-related information providing device 2 is connected to a local network 10 inside an operating room via a connection interface or the like. The operation-related information providing device 2 is electrically connected to a monitor 6, an audio microphone 11, an indoor camera 12, and the like. The monitor 6 is provided with a touch screen 7 and an eye gaze sensor 8. The processor 3 of the operation-related information providing device 2 causes generated data or the like to be displayed on the monitor 6. Information on the operation including operator-related information is input to the touch screen 7, the eye gaze sensor 8, the audio microphone 11, the indoor camera 12, and the like. For example, operator-related information and patient-related information is input to the touch screen 7 by the operator performing an operation. In addition, operator-related information is input to the eye gaze sensor 8, the audio microphone 11, the indoor camera 12, and the like through detection or observation of an operator's eye gaze, voice, movement, and the like. In an example, a lever or button operated by the operator may be provided as a member or device to which operator-related information is input; alternatively, another sensor for detecting an operator's movement may be provided. The processor 3 performs processing to be described later based on the operator-related information.

The system 1 includes an endoscope 13, a scope holder 15, an image processor 17, and a monitor 18. In the operation, the endoscope 13 is inserted into a body cavity, such as an abdominal cavity, from a port (hole) formed in a body wall of the subject (patient). The endoscope 13 is provided with an imaging element, such as a CCD, and the imaging element images an object inside the body cavity in the operation. In an example, a bending section, which is bendable, is provided in a portion of the endoscope 13 which is inserted into the body cavity. In another example, the bending section may not be provided. The scope holder 15 is mounted on, for example, a bed, and holds the endoscope 13. The scope holder 15 includes a mounting portion on which the endoscope 13 is mounted. In an embodiment, the scope holder 15 has an articulated structure and is, for example, a robotic arm having multiple joints.

The image processor 17 is electrically connected to the imaging element of the endoscope 13. The image processor 17 performs image processing on an object image imaged by the imaging element and generates an endoscope image of the object. In an example, the image processor 17 is electrically connected to a monitor 18. In this case, the image processor 17 causes the generated endoscope image to be displayed on the monitor 18. The image processor 17 is connected to the local network 10 via a connection interface or the like. The operation-related information providing device 2 exchanges information with the image processor 17 via the local network 10. For example, the operation-related information providing device 2 acquires the endoscope image generated by the image processor 17 and causes the acquired endoscope image to be displayed on the monitor 6.

The system 1 is provided with a drive source (not shown). Driving of the drive source actuates each of the joints of the scope holder 15, and thereby operates the scope holder 15. In an example, the aforementioned bending section is provided in the endoscope 13, and is bent by the drive source being driven. The position and posture of the endoscope 13 are changed by the operation of each of the scope holder 15 and the bending section. The drive source includes, but is not limited to, a motor, air pressure, oil pressure, water pressure, and an artificial muscle.

The system 1 includes a view controlling device 21 as a controlling device separate from the operation-related information providing device 2. The view controlling device 21 is provided with a processor, a storage medium, and the like, and is connected to the local network 10 via a connection interface or the like. Therefore, the operation-related information providing device 2 exchanges information with the view controlling device 21 via the local network 10. The processor and the like of the view controlling device 21 performs at least one of control of the view of the endoscope 13 and correction of the endoscope image based on, for example, the result of processing at the operation-related information providing device 2. Accordingly, the view controlling device 21 generates an optimum endoscope image in correspondence with the result of processing at the operation-related information providing device 2. In an example, by controlling the driving of the drive source, the view controlling device 21 adjusts the position and posture of the endoscope 13 and controls the view of the endoscope 13. In another example, the view controlling device 21 cuts a portion of the endoscope image generated by the image processor 17, thereby correcting the endoscope image. In an example, the operation-related information providing device 2 acquires information on drive control of the drive source by the view controlling device 21, and recognizes position information of the endoscope 13 based on the information on drive control of the drive source.

The system 1 includes an energy controlling device 22, a pneumoperitoneum-device controller 23, and vital equipment 25. The energy controlling device 22, the pneumoperitoneum controlling device 23, and the vital equipment 25 are each connected to the local network 10 via a connection interface. Therefore, the operation-related information providing device 2 exchanges information with each of the energy controlling device 22, the pneumoperitoneum-device controller 23, and the vital equipment 25 via the local network 10. In the operation, one or more treatment instruments (not shown) are inserted into the body cavity together with the endoscope 13. Depending on the treatment, an energy device capable of applying treatment energy to living tissue or the like may be used as a treatment instrument. The energy device is enabled to apply treatment energy to living tissue or the like by being supplied with electric energy from the energy controlling device 22. The energy controlling device 22 controls the output of electric energy to the energy device. The treatment instrument (hand instrument) including the energy device, and the endoscope 13 are surgical instruments used for an operation.

In an operation, the internal pressure (pneumoperitoneum pressure) of the body cavity is adjusted by a pneumoperitoneum device (not shown). The pneumoperitoneum-device controller 23 controls the driving of the pneumoperitoneum device. The vital equipment 25 measures vital information of the subject. The operation-related information providing device 2 acquires, via the local network 10, vital information measured by the vital equipment 25. The vital information includes a blood pressure, heart rate, respiratory rate, body temperature, and the like of the subject.

The operation-related information providing device 2 is electrically connected to one or more sensors 26. In an example, a position sensor is provided as the sensor 26 to detect the position of the endoscope 13 and/or the position of the treatment instrument. In an example, a spatial sensor to be disposed inside the body cavity is provided as the sensor 26, and senses the internal space of the body cavity, which includes the type and placement of an organ, the distance to the abdominal wall, and the like. Accordingly, based on the detection results of the sensor 26, the operation-related information providing device 2 acquires the position information of the surgical instruments, including the endoscope 13 and the treatment instrument, and the space information on the inside of the body cavity. In an example, detection, measurement, or observation is performed by a device, such as the indoor camera 12, disposed outside the body cavity. In the operation, the operation-related information providing device 2 acquires information on the outside of the body cavity, that is, information on the operating room, based on the detection result, measurement result, or observation result at the device such as the room camera 12. At this time, the operation-related information providing device 2 acquires, as the information on the outside of the body cavity, information on the port into which the surgical instruments including the endoscope 13 and the treatment instrument are inserted and the types of the surgical instruments inserted from the port.

The system 1 includes a processing device 27, such as a PC. The processing device 27 is connected to the local network 10 via a connection interface. Therefore, the operation-related information providing apparatus 2 exchanges information with the processing device 27 via the local network 10. The operator performs processing using software stored in the storage medium or the like of the processing device 27 or software introduced from a storage medium, such as a USB memory, externally attached to the processing device 27. For example, before an operation, the operator performs simulation of the operation using the processing device 27, and creates an operation plan including a procedure.

In the system 1, the local network 10 is connected to an integrated network 30 outside the operating room via a connection interface. An integrated monitor 31 and database 33 are each connected to the integrated network 30 via a connection interface. The operation-related information providing device 2 exchanges information with the integrated monitor 31 and the database 33 via the local network 10 and the integrated network 30, respectively. In an example, the processor 3 of the operation-related information providing device 2 causes the generated information, data, and the like to be displayed on the integrated monitor 31. The database 33 stores many types of data in the medical field. In an example, the processor 3 of the operation-related information providing device 2 searches the database 33 for required data and acquires the required data from the database 33.

FIG. 2 shows processing performed by the processor 3 of the operation-related information providing device 2. As shown in FIG. 2, the processing performed by the processor 3 (S100) includes processing performed before the operation (S101) and processing performed during the operation (S102). As the processing performed in the operation, the processor performs generation of real-time data (S103) and navigation (S104). In an example, as the processing performed in the operation, the processor 3 performs not only processing of S103 and S104, but also at least one of navigation relating to bleeding position (S105), display of pre-operation data (S106), notification of vital information (S107), notification of a real-time task (S108), notification of risk (S109), notification of recommended information (S110), judgment of re-planning of the operation (S111), and selection of information to be displayed (S112). Hereinafter, each type of processing performed by the processor 3 will be described.

[Processing Performed Before Operation (S101)]

Figure 3:
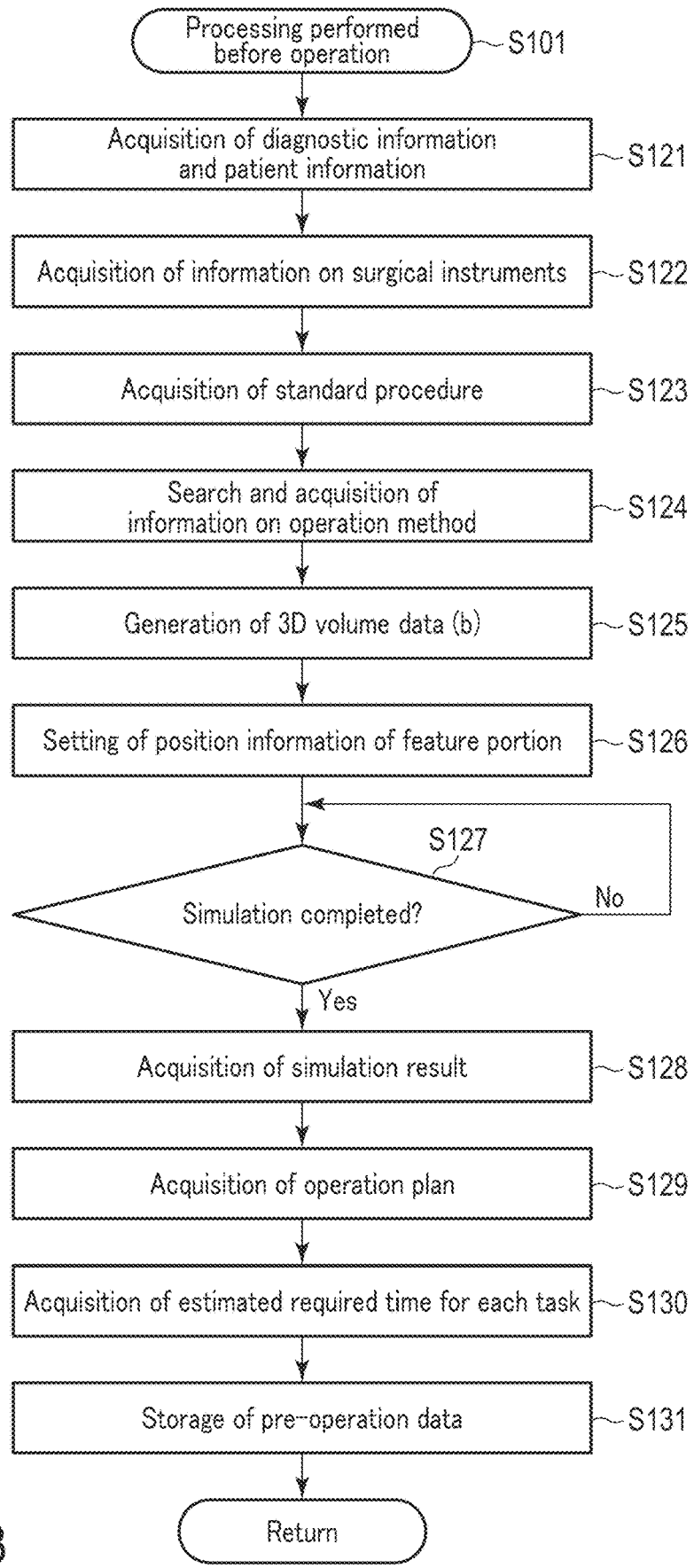
FIG. 3 is a flowchart showing processing performed before an operation by the processor of the operation-related information providing device according to an exemplary embodiment.

Before the operation, the operator or the like creates an operation plan including a procedure in the operation, using for example, the processing device 27. Before the operation, the processor 3 acquires the created operation plan or the like as pre-operation data. FIG. 3 shows processing performed by the processor 3 before the operation. As shown in FIG. 3, the processor 3 acquires diagnostic information and patient information before the operation (S121). The diagnostic information includes a CT image, an MRI image, and medical record information. The patient information may include information on the risk when the operation is performed, such as medical history, medication being taken, and health condition. Subsequently, the processor 3 acquires information on surgical instruments, such as the treatment instrument, endoscope 13, and the like, used for the operation (S122). The processor 3 then acquires a standard procedure (protocol) for the operation to be performed (S123). The processor 3 then searches for and acquires information on operation methods of the operation to be performed (S124). At this time, the processor 3, for example, searches the database 33 for information for a wide search of operation methods or the like for the disease of the subject.

The processor 3 then generates 3D volume data of the inside of the body cavity of the subject based on the information acquired from S121 to S124 (S125). Namely, 3D volume data is generated before the operation from information on the subject, and the like. In, for example, FIG. 3, the 3D volume data generated before the operation is referred to as "3D volume data (b)". The processor 3 then recognizes a feature portion of the inside of the body cavity in the generated 3D volume data. The processor 3 then sets position information of the recognized feature portion in the 3D volume data (S126). The processor 3 thereby generates and acquires, before the operation, position information of the feature portion of the inside of the body cavity. The feature portion includes, for example, a vessel (blood vessel and lymph vessel), an organ, a nerve, a tumor, and a lymph node. The processor 3 also recognizes, as a feature portion, at least one of the portion that needs to be recognized in the operation and the position that may cause risk in the operation. In an example, the processor 3 recognizes a feature portion in the generated 3D volume data based on a result of learning using AI. In another example, the processor 3 recognizes a feature portion in the generated 3D volume data based on an instruction from the operator or the like.

Upon generation of the 3D volume data and setting of the position information of the feature portion, the operator performs simulation of the operation on the generated 3D volume data. The simulation is performed before the operation by means of the processing device 27. When performing the simulation, for example the processor 3 outputs the 3D volume data generated in S125 and the position information of the feature portion set in S126 to the processing device 27. The simulation includes simulation relating to incision, simulation relating to anastomosis, simulation relating to an approach to the affected area, simulation relating to pressure exhaust of the organ, and simulation relating to the view of the endoscope 13 on the operative field. For example, an incision line in the operation is determined in the simulation relating to incision, and an anastomosis position in the operation is determined in the simulation relating to anastomosis.

After completing the simulation using the processing device 27 (Yes in S127), the processor 3 of the operation-related information providing device 2 acquires a result of the simulation performed before the operation (S128). Then, the processor 3 acquires an operation plan including a procedure in the operation (S129). Upon completion of the simulation and creation of the operation plan, the processor of the processing device 27 estimates a required time for each of the tasks of the procedure. The processor 3 then acquires the estimated required time for each of the tasks from the processing device 27 (S130).

In an example, upon creation of the operation plan, the operator or the like estimates a required time for each of the tasks. In this case, the operator inputs the estimated required time for each of the tasks to the operation-related information providing device 2 by, for example, operating the touch screen 7.

Then, the processor 3 stores the information or the like acquired by the processing from S121 to S130 as pre-operation data (S131). The pre-operation data may be stored in the storage medium 5 of the operation-related information providing device 2, or may be stored in the storage medium of the processing device 27. The stored pre-operation data enables the processor 3 to acquire the position information of the feature portion of the inside of the body cavity of the subject, which is generated before the operation, and the procedure or the like in the operation, which is planned before the operation.

The operator may use the processing device 27 to not only perform the aforementioned simulation, but to also determine a treatment instrument used for the operation. The operator may use the processing device 27 to also determine adjustment values in the operation which relates to surgical instruments including the endoscope 13 and the treatment instrument. In this case, the processor 3 acquires the type of the determined treatment instrument, the determined adjustment values, and the like as the pre-operation data.

In an example, a procedure is planned for each operation scene in the aforementioned creation of the operation plan. A detailed plan is created for each of the tasks constituting the procedure. In an example, the processor 3 acquires a patient's body mass index (BMI) as patient information. The optimum operation plan is made based on the acquired BMI and the like. In an example, simulation relating to the position of a trocar is performed in the simulation. For example, in the case of gastric bypass surgery, a resection site is determined in the simulation. Then, the position of a trocar is determined in the simulation to create a state where the determined resection site can be easily resected. The simulation relating to the position of a trocar is performed for, for example, an operation with high anatomic specificity. In an example, an operation to remove rectal cancer is performed, and the processor 3 acquires information on the remnant in the rectum before the operation as pre-operation data in addition to the aforementioned information.

In an example, in generation of position information of a plurality of lymph nodes, the processor 3 performs numbering and recognizes each of the lymph nodes. In an example, the processor 3 generates position information of the feature portion in consideration of the positional relationship with a nerve or the like which is highly likely to induce a complication. In an example, in determination of an incision line in simulation relating to incision or the like, an incision line in a patient's body wall (body surface) and the placement of a trocar are determined. In an example, the processor 3 recognizes the incision line, anastomosis position, and the like determined in the simulation as feature portions in the 3D volume data generated in S125. The processor 3 then sets position information of the incision line, anastomosis position, and the like in the 3D volume data. For example, in the case of gastric bypass surgery, the anastomosis position at the time of cutting the stomach is determined by simulation. In this case, the processor 3 sets position information of the determined anastomosis position in the 3D volume data. In an example, the processor 3 judges before the operation whether or not the surgical instruments to be used are in a normal state from information on the surgical instruments or the like. If it is judged that there is a problem with the surgical instruments to be used, the processor 3 causes notification to be provided before the operation.

As described above, an appropriate operation plan is created in correspondence with patient information or the like by the processing performed by the processor 3 before the operation and the simulation performed by means of the processing device 27. Collective handling of patient information is also enabled. The operation plan may be created based on information on risk incurred when the operation is performed, which is included in the patient information. In this case, the operation plan is created in consideration of the resection range and other precautions. Moreover, the above-described creation of the operation plan facilitates selection of the optimum operation method for the operation to be performed, the optimum type of treatment instruments, the optimum adjustment values for the surgical instruments, and the like. Because the operation plan is created in the manner described above, a safe operation plan is created.

[Generation of Real-Time Data (S103) and Navigation (S104)]

Figure 4:
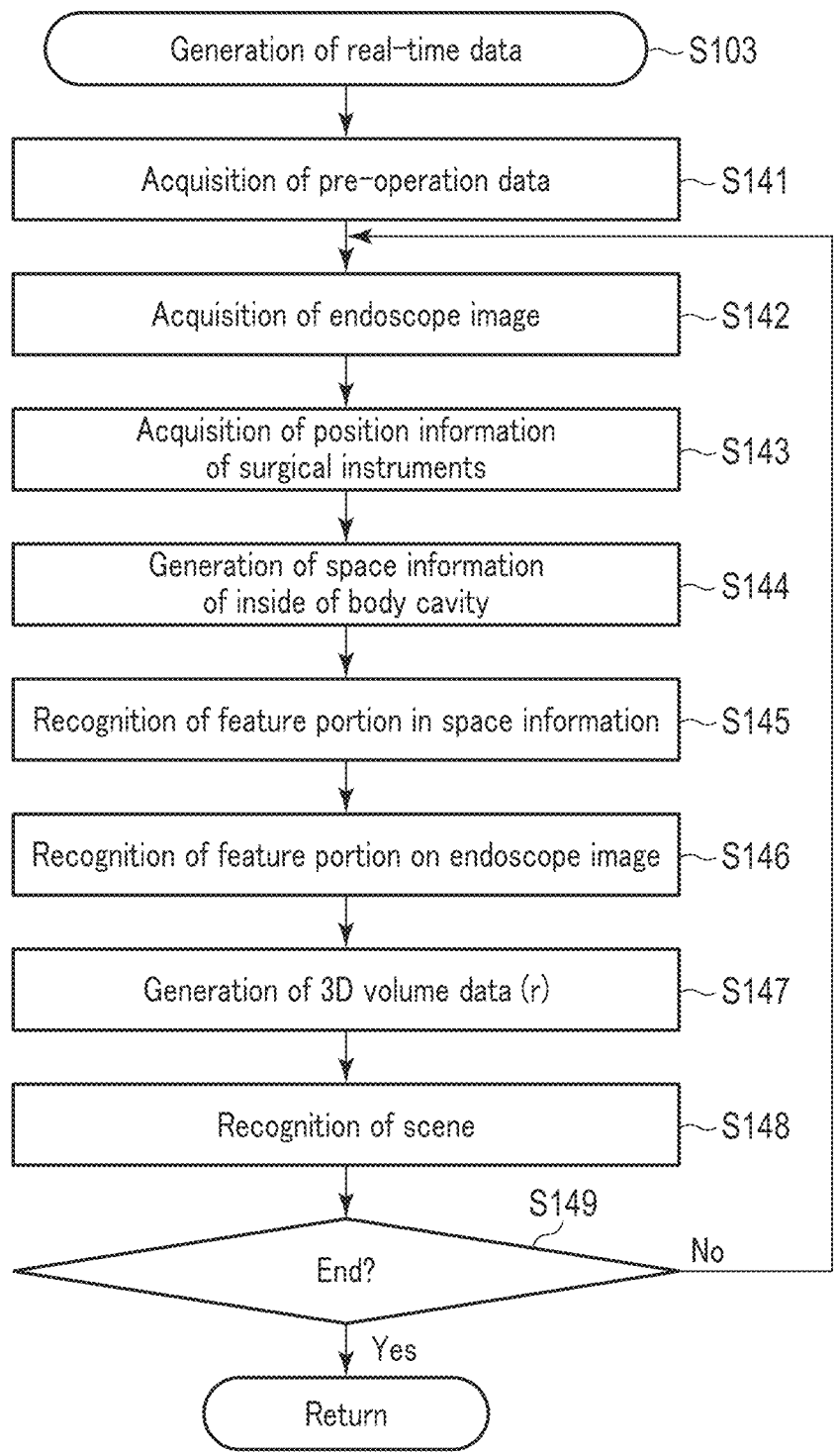
FIG. 4 is a flowchart showing processing performed in generation of real-time data by the processor of the operation-related information providing device according to an exemplary embodiment.

In the operation using the system 1, the endoscope 13 is inserted into the body cavity, and the inside of the body cavity is observed. The image processor 17 then generates an endoscope image. The processor 3 of the operation-related information providing device 2 then generates real-time data based on the aforementioned pre-operation data, the endoscope image, and the like. FIG. 4 shows processing performed by the processor 3 in the generation of real-time data. As shown in FIG. 4, the processor 3 acquires the aforementioned pre-operation data in the operation (S141). The processor 3 then acquires a real-time endoscope image (S142). The processor 3 then acquires real-time position information of the surgical instruments including the endoscope 13 and the treatment instrument (S143). At this time, the processor 3 acquires position information of the surgical instruments based on detection results or the like at the sensor 26 provided as a position sensor. The processor 3 may also recognize position information of the endoscope 13 based on information on the drive control of the drive source by the view controlling device 21.

The processor 3 also acquires the following information in real time, not shown in FIG. 4. That is, the processor 3 acquires real-time detection results at the sensor 26 provided as a spatial sensor inside the body cavity. The processor 3 acquires real-time vital information of the patient from the vital equipment 25. The processor 3 acquires real-time information on the outside of the body cavity based on information from a device, such as the indoor camera 12, disposed outside the body cavity. The processor 3 acquires real-time information on the operator from the touch screen 7, the eye gaze sensor 8, the audio microphone 11, the indoor camera 12, and the like.

The processor 3 acquires a real-time three-dimensional shape of the inside of the body cavity based on the endoscope image, the position information of the surgical instruments, and the detection results at the sensor 26 inside the body cavity. The processor 3 then generates real-time space information on the inside of the body cavity based on the acquired three-dimensional shape (S144). At this time, the processor 3 generates, for example, 3D surface data as the real-time space information. By generating the space information, the processor 3 generates real-time position information and posture information of the surgical instruments, including the endoscope 13 and the treatment instrument inside the body cavity.

In the generated space information, the processor 3 recognizes the aforementioned feature portion (S145). The processor 3 also recognizes the aforementioned feature portion on the endoscope image (S146). The recognition of the feature portion on the endoscope image is performed only for the feature portion shown in the endoscope image. In the recognition of the feature portion, the processor 3 recognizes not only the vessel (blood vessel and lymph vessel), an organ, a nerve, a tumor, a lymph node, and the like, but also the incision line and anastomosis position determined in the simulation. In the case where a treatment instrument is present in the endoscope image, the processor recognizes the treatment instrument on the endoscope image. In an example, the processor 3 recognizes the feature portion and the treatment instrument on the endoscope image based on a result of learning using AI.

The processor 3 then converts the 3D volume data acquired as pre-operation data, based on the endoscope image and the generated space information (3D surface data). Accordingly, the processor 3 generates real-time 3D volume data (S147). The real-time 3D volume data is included in the real-time data, and is referred to as "3D volume data (r)" in FIG. 4, etc. Since the real-time 3D volume data is generated as described above, the processor 3 also recognizes the feature portion in the real-time 3D volume data. That is, the real-time 3D volume data includes real-time position information of the aforementioned feature portion, and the real-time position information of the feature portion is generated through generation of the real-time 3D volume data.

The processor 3 than recognizes a real-time scene (operation scene) based on the real-time 3D volume data, vital information, information on the outside of the body cavity, information on the operator, and the like (S148). At this time, the processor 3 recognizes the real-time scene, based on not only the aforementioned information but also the pre-operation data including the procedure planned before the operation. In the recognition of the real-time scene, the processor 3 also utilizes information stored in the database 33. In an example, the processor 3 recognizes the real-time scene based on a result of learning using AI.

Unless the processor 3 decides to terminate the processing of S103 (No in S149), the processing returns to S142. Then, the processor 3 sequentially performs the processing from S142 onward. Thus, the processor 3 continuously generates real-time 3D volume data and continuously recognizes the real-time scene as long as the processing of S103 is being performed. That is, the real-time data is updated as long as the processing of S103 is being performed. In an example, the processor 3 continues the processing of S103 as long as the real-time endoscope image, real-time position information of the surgical instruments, and the like is being acquired.

In the operation, the processor 3 performs the navigation of S104 based on the real-time data generated in S103. In the navigation, the processor 3 generates a navigation image (an image) which is displayed on the endoscope image in a superimposed manner. Therefore, the processor 3 performs generation of real-time data of S103 when performing the navigation of S104. The processor 3 performs the navigation during a period between an instruction to start the navigation to an instruction to stop the navigation. The instruction to start the navigation and the instruction to stop the navigation may be provided by a voice of the operator or the like through the audio microphone 11 or the like or by an operation of the touch screen 7 or the like by the operator or the like.

Figure 5:
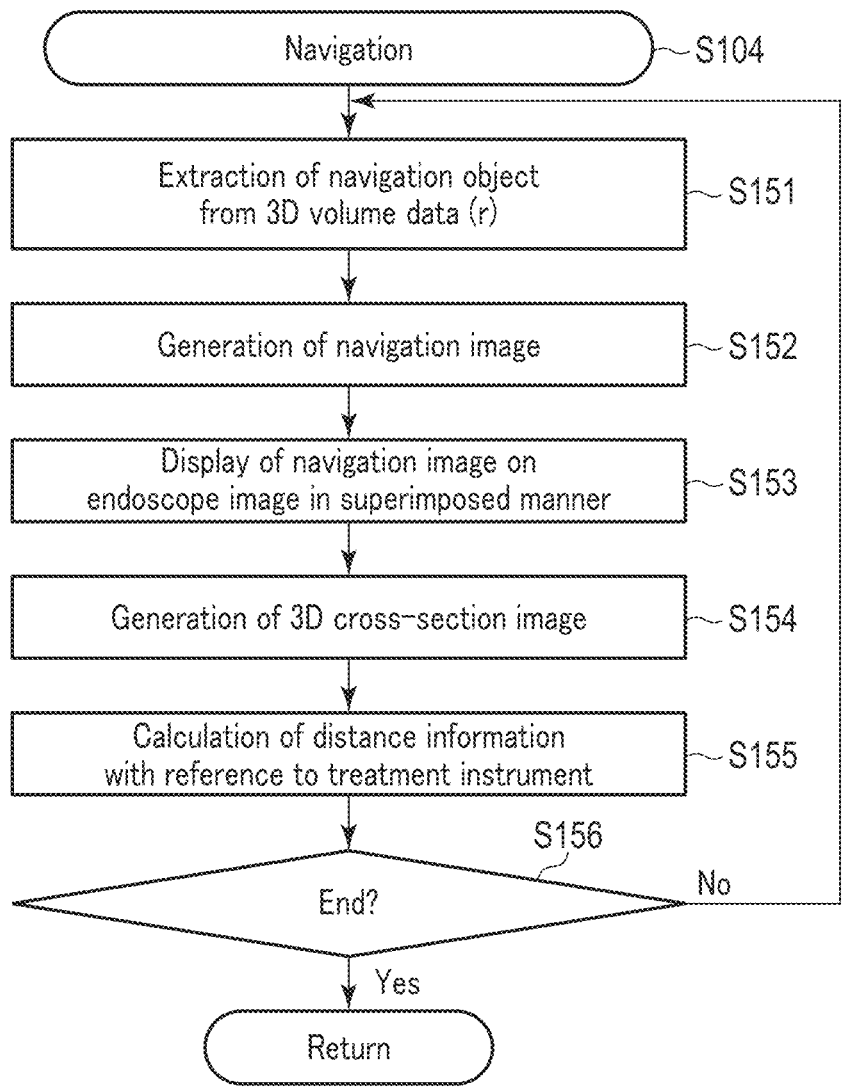
FIG. 5 is a flowchart showing processing performed in navigation by the processor of the operation-related information providing device according to an exemplary embodiment.

FIG. 5 shows processing performed by the processor 3 in the navigation. As shown in FIG. 5, the processor 3 recognizes a navigation object in the real-time 3D volume data in the navigation. The processor 3 then extracts the navigation object from the real-time 3D volume data (S151). The navigation object is, for example, at least part of the aforementioned feature portion, and is any one of a vessel, such as a blood vessel, a ureter, or a bile duct, an anastomosis position, an incision line, a tumor, a lymph node, a nerve, and the like. The navigation object is designated by the operator or the like in the operation. In an example, upon receipt of an instruction to start the navigation, the processor 3 causes 3D volume data (3D volume data (b)) acquired as pre-operation data or real-time 3D volume data (3D volume data (r)) to be displayed on the monitor 6 or the like. At this time, the processor 3, for example, converts the 3D volume data into two-dimensional image information and displays the converted data. The operator then designates a navigation object from the displayed 3D volume data.

Upon extraction of the navigation object from the 3D volume data (3D volume data (r)) as described above, the processor 3 generates a navigation image using the extracted navigation object (S152). At this time, the processor 3 generates a navigation image by converting the navigation object into two-dimensional image information. Since the navigation image is generated as described above, a navigation image corresponding to real-time position information of the navigation object is generated. The processor 3 then causes the generated navigation image to be displayed on the endoscope image in a superimposed manner (S153).

In an example, based on the real-time 3D volume data, real-time position information of the treatment instrument, and pre-operation data, the processor 3 generates a 3D cross-section image showing a cross section corresponding to the real-time position of the treatment instrument (S154). The processor 3 then causes the generated 3D cross-section image to be displayed on the monitor 6 or the like. In this case, the processor 3 may cause the real-time position information of the navigation object to be displayed on the 3D cross-section image in a superimposed manner. In an example, the processor 3 calculates real-time distance information with reference to the treatment instrument, based on the real-time 3D volume data, real-time position information of the treatment instrument, and pre-operation data. In this case, the processor 3 may cause the calculated distance information to be displayed. When the navigation object is displayed on the endoscope image, the processor 3 recognizes the navigation object in the endoscope image. The processor 3 then causes a navigation image for the recognized navigation object to be displayed on the endoscope image in a superimposed manner.

Unless the processor 3 decides to terminate the processing of S104 (No in S156), the processing returns to S151. Then, the processor 3 sequentially performs the processing from S151 onward. Therefore, the processor 3 updates the navigation image as long as the processing of S104 is being performed until, for example, an instruction is received to stop the navigation.

Figure 6:
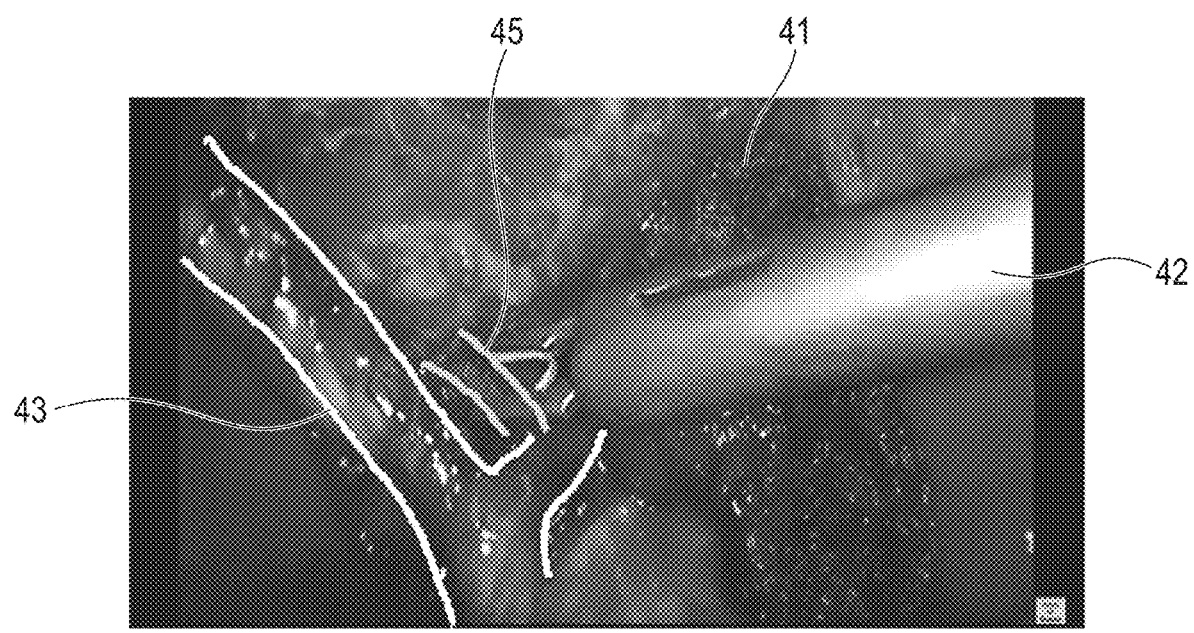
FIG. 6 is a diagram showing an example of the state where navigation images are displayed on an endoscope image in a superimposed manner in an exemplary embodiment.

FIG. 6 shows an example of the state where a navigation image is displayed on an endoscope image 41 in a superimposed manner. In the example of FIG. 6, a treatment instrument 42 is shown in the endoscope image 41. A blood vessel navigation image 43 and a nerve navigation image 45 are displayed on the endoscope image 41 in a superimposed manner. The blood vessel and nerve that are navigation objects are not shown in the endoscope image. In the image of FIG. 6, the navigation images 43 and 45 enable confirmation of position information or the like of a nerve or blood vessel, which is an anatomical structure that cannot be observed only by the endoscope image 41.

In an example, observation with the endoscope 13 is performed by an indocyanine green (ICG) fluorescence method. The processor 3 then recognizes light emission information including a real-time light emission position of ICG in the organ, and generates a navigation image indicating the light emission information of ICG. In fact, the ICG gradually becomes difficult to recognize in the endoscope image or the like as the ICG diffuses little by little. Therefore, even if ICG penetrates into the peripheral tissue and becomes difficult to recognize in the endoscope image or the like, the operator can confirm the range of ICG before diffusion through the navigation image showing the light emission information of ICG. In an example, the processor 3 visualizes a blood vessel and a tumor as navigation objects, and also generates a navigation image for a sentinel lymph node. Accordingly, the sentinel lymph node is also visualized.

In an example, a specific portion in an organ or the like is registered as a Merkmal. The processor 3 then recognizes the portion registered as a Merkmal as a feature portion, and generates a navigation image for the portion registered as a Merkmal. In an example, the processor 3 causes a name or the like of the portion for which a navigation image was generated to be displayed together with the navigation image. In an example, the resection area of the liver, the resection area of the colon, and the resection area in gastric bypass surgery are determined before the operation. The processor 3 then generates navigation images of these resection areas. In an example, the processor 3 visualizes the suture position determined before the operation as a navigation object.

In an example, total hysterectomy surgery is performed, in which the vagina is cut from the uterus, and the vaginal stump, which is the cut position, is sutured. In this case, the processor 3 recognizes the real-time position information of the vaginal stump after the vagina is cut from the uterus. The processor 3 then visualizes the vaginal stump as a navigation object. In an example, suturing, such as suturing of the aforementioned vaginal stump, is performed. After the suturing, the processor 3 recognizes the real-time blood flow and visualizes information on the blood flow. In this example, the processor 3 may determine the next insertion point of the needle for suturing based on the real-time blood flow. In this case, the processor 3 generates a navigation image of the determined insertion point, and visualizes the insertion point. This allows a needle to be inserted at an appropriate position in suturing, and effectively prevents a complication or the like after the operation.

In an example, an operation for rectal cancer is performed. The processor 3 recognizes real-time position information of the remnant in the cleaning of the large intestine, and generates a navigation image of the remnant. In an example, after the bladder and urethra are anastomosed, the processor 3 recognizes real-time position information of the anastomosis position between the bladder and urethra. The processor 3 generates a navigation image of the recognized anastomosis position.

By performing the above-described processing, the processor 3 appropriately recognizes the real-time position information of the feature portion. The processor 3 thereby appropriately generates real-time 3D volume data including the real-time position information of the feature portion. That is, the processor 3 generates appropriate real-time data. Thus, the processor 3 appropriately presents information relating to the feature portion in real time. In addition, the scene is recognized based on the appropriate real-time data; therefore, the real-time scene is appropriately recognized by the processor 3.

By performing the above-described processing, the processor 3 extracts a navigation object based on the real-time 3D volume data appropriately generated. Therefore, the processor 3 properly recognizes the real-time position information or the like of the navigation object. Accordingly, the processor 3 generates an appropriate navigation image, and causes the navigation object to be appropriately superimposed on the endoscope image based on the real-time position information of the navigation object. This enables the operator or the like to appropriately perform an operation based on a navigation image that is appropriately displayed in a superimposed manner, thereby improving the degree of safety of the operation.

Further, since the above-described processing is performed by the processor 3, the navigation image enables the operator to recognize an anatomical structure (vascular, tumor, or the like) that is not shown on the endoscope image. Therefore, the operator can perform an operation while confirming an anatomical structure that cannot be observed from the endoscope image alone. This effectively prevents unintended damage to an organ or the like. Further, since the above-described processing is performed by the processor 3, the navigation image enables the operator to confirm the incision line, anastomosis position, and the like determined before the operation.

[Navigation Relating to Bleeding Position (S105)]

In an example, the processor 3 performs not only the processing of S103 and S104, but also navigation relating to the bleeding position (S105) in the operation. The processor 3 performs navigation of the bleeding position while recognizing bleeding on the endoscope image. Therefore, when the processor 3 does not recognize bleeding on the endoscope screen, such as when bleeding does not occur within the range of the endoscope image, the processor 3 does not perform navigation of the bleeding position.

Figure 7:
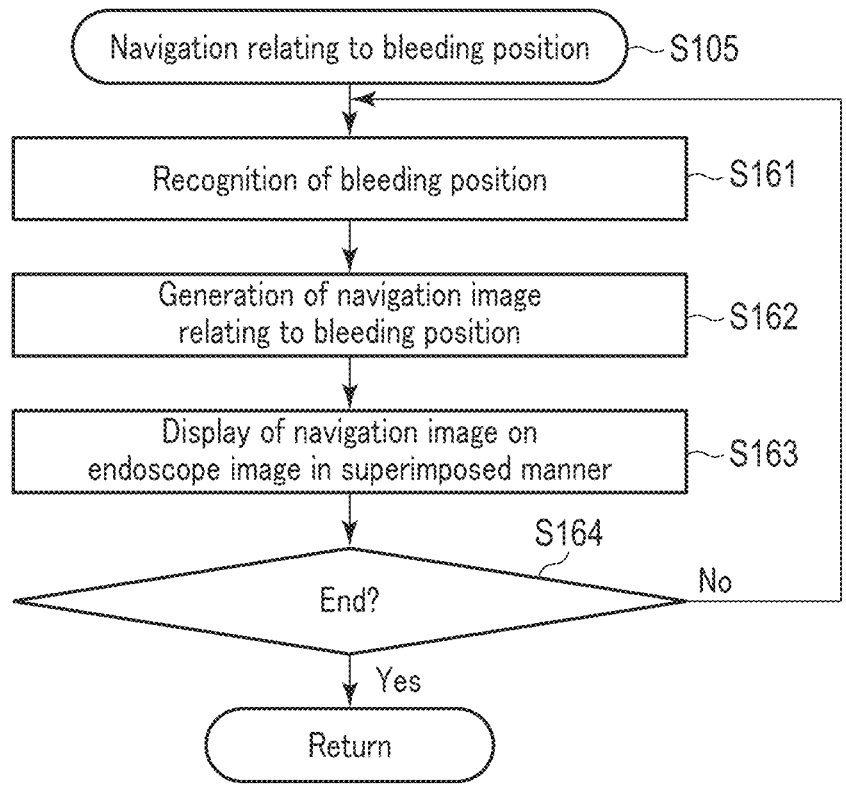
FIG. 7 is a flowchart showing processing performed in navigation relating to a bleeding position by the processor of the operation-related information providing device according to an exemplary embodiment.

FIG. 7 shows processing performed by the processor 3 in the navigation relating to the bleeding position. As shown in FIG. 7, in the navigation of the bleeding position, the processor 3 recognizes the real-time bleeding position in the endoscope image (S161). In this case, the processor 3 may recognize the bleeding position in the real-time 3D volume data generated in the processing of S103. The processor 3 then generates a navigation image relating to the bleeding position (S162), and causes the generated navigation image to be displayed on the endoscope image in a superimposed manner (S163).

Unless the processor 3 decides to terminate the processing of S105 (No in S164), the processing returns to S161. Then, the processor 3 sequentially performs the processing from S161 onwards. Therefore, as long as the processing of S105 is being performing, for example as long as bleeding is recognized on the endoscope image, the processor 3 continues to generate a navigation image relating to the bleeding position.

When the bleeding position is buried under blood, the processor 3 generates a navigation image so that the operator can recognize the bleeding position in the puddle of blood. In this case, the processor 3 may recognize the real-time depth from the surface of the puddle of blood to the bleeding position, and cause the recognized depth to be displayed. In an example, the processor 3 recognizes the real-time amount of bleeding from the bleeding position and the real-time state of the neighborhood of the bleeding position. The processor 3 then estimates an appropriate hemostatic method based on the recognized amount of bleeding and the state of the neighborhood of the bleeding position. In an example, a judgment is made as to the type of the energy device to be used for hemostasis, the position to be compressed, and the like in the estimation of the hemostatic method. In the judgment of the type of the energy device, it is judged whether or not an energy device used in real time is appropriate. In the estimation of the hemostatic method, it is also judged which of suctioning and water supply (flushing by water) should be given a higher priority in hemostasis.

The above-described navigation relating to the bleeding position by the processor 3 enables the operator to immediately recognize bleeding and the bleeding position. This enables immediate hemostasis.

[Display of Pre-Operation Data (S106)]

Figure 8:
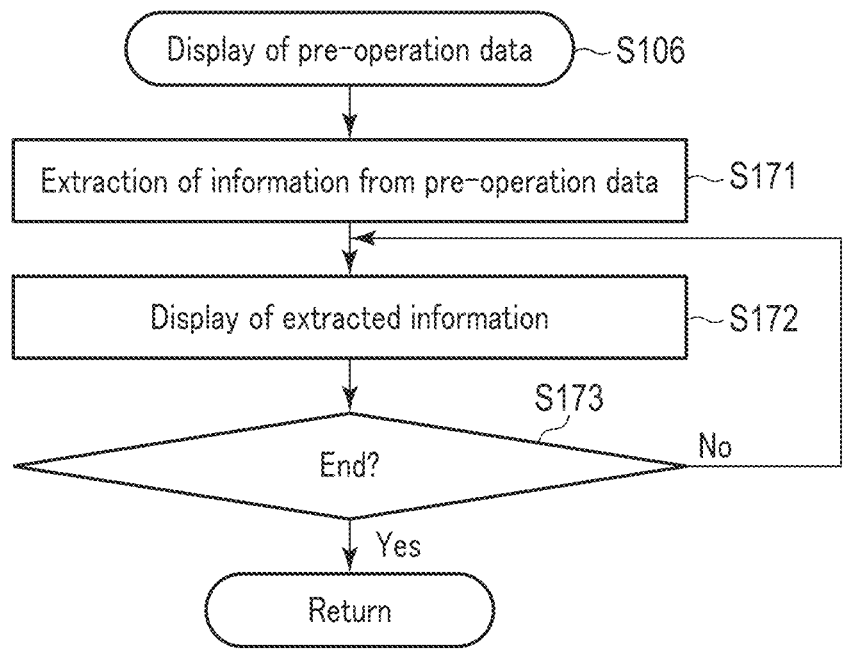
FIG. 8 is a flowchart showing processing performed in display of pre-operation data by the processor of the operation-related information providing device according to an exemplary embodiment.

In an example, the processor 3 performs not only the processing and the like of S103 and S104, but also display of pre-operation data (S106). In the display of the pre-operation data, the processor 3 uses the pre-operation data acquired by the processing of S103. FIG. 8 shows processing performed by the processor 3 in the display of the pre-operation data. As shown in FIG. 8, in the display of the pre-operation data, the processor 3 extracts some information to be displayed from the pre-operation data (S171). The processor 3 then generates an image for the extracted information. The processor 3 then causes an image showing the information extracted from the pre-operation data to be displayed together with the endoscope image (S172). The data to be displayed is, for example, a diagnostic image, such as a CT image or MRI image, before the operation, a result of simulation performed before the operation, 3D volume data generated before the operation, and patient information or the like before the operation.

Unless the processor 3 decides to terminate the processing of S106 (No in S173), the processing returns to S172. Then, the processor 3 sequentially performs the processing from S172 onward. Therefore, the processor 3 causes information extracted from the pre-operation data to be displayed as long as the processing of S106 is being performed. In an example, the processor 3 judges whether or not to perform the display of the pre-operation data, based on either an instruction by the operator or the like or the real-time scene recognized in the processing of S103. In an example, the processor 3 determines information to be extracted from the pre-operation data, based on either an instruction by the operator or the like or the real-time scene recognized in the processing of S103. In this case, the processor 3 judges which type of the pre-operation data should be displayed, based on either an instruction by the operator or the like or the real-time scene.

Figure 9:
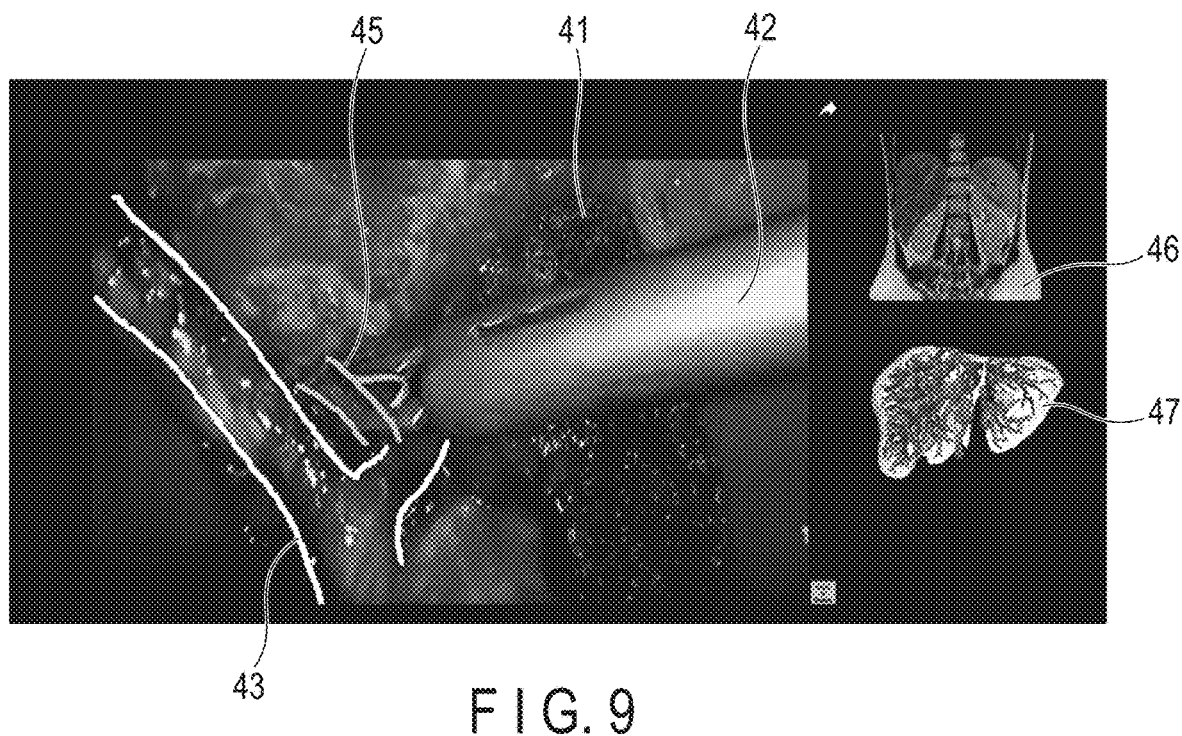
FIG. 9 is a diagram showing an example of the state where some information of the pre-operation data is displayed together with the endoscope image in an exemplary embodiment.

FIG. 9 shows an example of the state where some information of the pre-operation data is displayed together with the endoscope image. In the example of FIG. 9 also, the navigation images 43 and 45 are displayed on the endoscope image 41 in a superimposed manner. In the image of FIG. 9, a CT image 46 before the operation and a result of simulation performed before the operation are also displayed together with the endoscope image. The above-described display of the pre-operation data by the processor 3 enables the operator to confirm, in the operation, the operation plan created before the operation.

[Notification of Vital Information (S107)]

Figure 10:
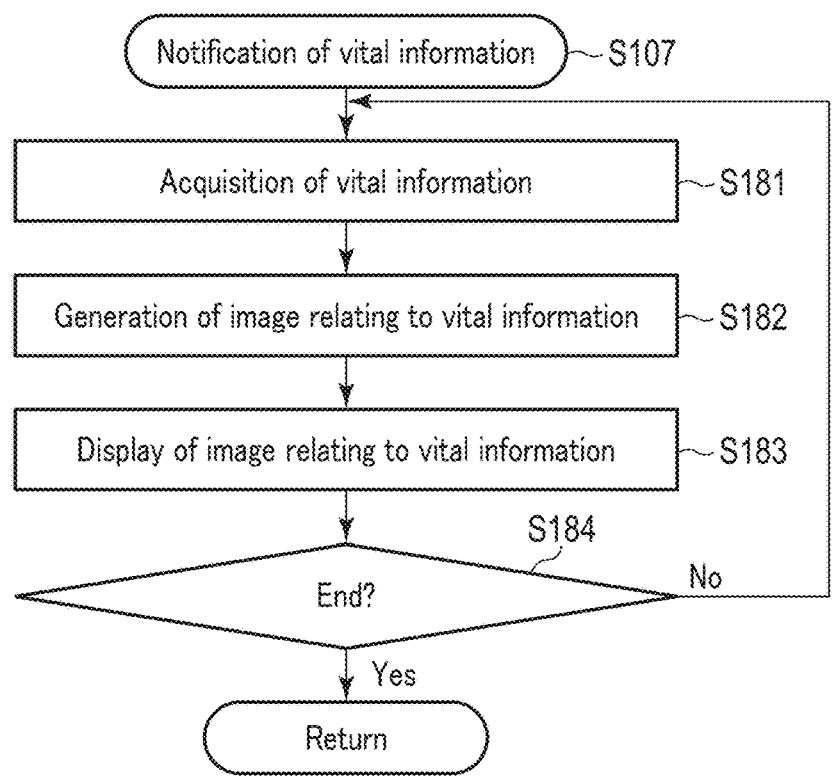
FIG. 10 is a flowchart showing processing performed in notification of vital information by the processor of the operation-related information providing device according to an exemplary embodiment.

In an example, the processor 3 performs not only the processing and the like of S103 and S104, but also notification of vital information, such as a blood pressure, heart rate, and the like of the patient (S107). FIG. 10 shows processing performed by the processor 3 in the notification of vital information. As shown in FIG. 10, the processor 3 acquires real-time vital information measured by the vital equipment 25 in the notification of vital information (S181). The processor 3 then generates an image relating to the acquired vital information (S182). The processor 3 then causes the image relating to the vital information to be displayed together with the endoscope image (S183). In an example, the processor 3 causes some vital information, for example, the heart rate, to be reported by voice instead of image display.

Unless the processor 3 decides to terminate the processing of S107 (No in S184), the processing returns to S181. Then, the processor 3 sequentially performs the processing from S181 onward. Therefore, the processor 3 causes real-time vital information to be reported as long as the processing of S107 is being performed. Namely, as long as the processing of S107 is being performed, the vital information to be reported is updated. In an example, the processor 3 judges whether or not to perform notification of vital information, based on either an instruction by the operator or the like or the real-time scene recognized in the processing of S103. In an example, the processor 3 determines which of the vital information is to be reported, based on either an instruction by the operator or the like or the real-time scene recognized in the processing of S103.

FIG. 11 shows an example of the state where vital information is displayed together with the endoscope image. In the example of FIG. 11 also, the navigation images 43 and 45 are displayed on the endoscope image 41 in a superimposed manner. In the image of FIG. 11, an image 48 relating to vital information is displayed together with the endoscope image 41. The above-described notification of vital information by the processor 3 enables the operator to recognize real-time vital information of the subject in the operation.

In an example, the processor 3 can recognize a rapid change in vital information. In this example, when a rapid change in vital information is recognized, the processor 3 judges that there is a high probability of causing risk and causes a warning to be issued. In an example, the processor causes a warning to be issued when vital information deviates from an acceptable range. In an example, the processor 3 acquires not only real-time vital information, but also a real-time abdominal pressure. The processor 3 then reports the acquired abdominal pressure by screen display or the like.

[Notification of Real-Time Task (S108)]

In an example, the processor 3 performs not only the processing and the like of S103 and S104, but also notification of a real-time task (S108). In the operation, the processor 3 performs notification of a real-time task based on the real-time scene recognized in S103. Therefore, when performing the notification of a real-time task of S108, the processor 3 performs generation of real-time data of S103 in parallel.

FIG. 12 shows processing performed by the processor 3 in the notification of a real-time task. As shown in FIG. 12, in the notification of a real-time task, the processor 3 causes a procedure planned before the operation to be displayed in a flow chart form (S191). At this time, the procedure is displayed together with the endoscope image. The processor 3 recognizes a real-time task from a plurality of tasks in the procedure, based on the real-time scene recognized in the processing of S103 (S192). The processor 3 then highlights the recognized real-time task in the displayed procedure (S193).

Unless the processor 3 decides to terminate the processing of S108 (No in S194), the processing returns to S192. The processor 3 then sequentially performs the processing from S192 onward. Therefore, the processor 3 causes a real-time task to be displayed as long as the processing of S108 is being performed. That is, as long as the processing of S108 is being performed, the task to be highlighted is updated. In an example, the processor 3 judges whether or not to perform the notification of a real-time task, based on either an instruction by the operator or the like or the real-time scene recognized in the processing of S103.

Figure 13:
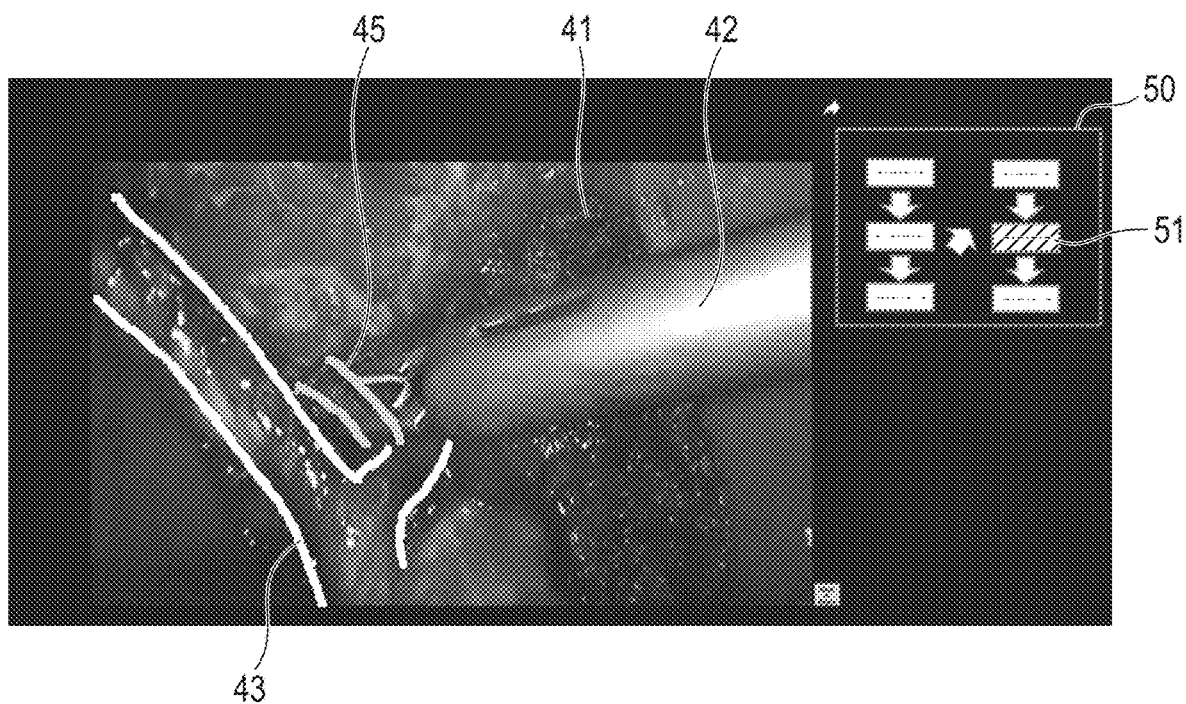
FIG. 13 is a diagram showing an example of the state where a procedure planned before the operation is displayed together with the endoscope image in an exemplary embodiment.

FIG. 13 shows an example of the state where the procedure planned before the operation is displayed together with the endoscope image. In the example of FIG. 13 also, the navigation images 43 and 45 are displayed on the endoscope image 41 in a superimposed manner. In the image of FIG. 13, a flowchart 50 indicative of the procedure planned before the operation is displayed together with the endoscope image 41. In the image of FIG. 13, a real-time task 51 is highlighted in comparison with the other tasks in the flowchart 50.

In an example, the processor 3 estimates a time elapsed from the start of the operation, based on an estimated required time for each of the tasks acquired as pre-operation data and the real-time scene (task). The processor 3 then estimates required times to complete the operation and to complete the real-time task based on the time elapsed from the start of the operation. The processor 3 then causes the estimated elapsed time and the required times to be displayed. In an example, the processor 3 causes information planned before the operation for the real-time task to be reported. In this case, the type of the treatment instrument used in the real-time task, the adjustment values for the surgical instruments in the real-time task, and the like are reported.

In an example, the processor 3 causes details of preparation necessary for the task subsequent to the real-time task to be reported by screen display or the like. In an example, the processor 3 causes detailed information on one given task of the tasks of the procedure to be reported by screen display or the like. In this case, the task detailed information of which is reported is designated by the operator or the like.

The above-described processing by the processor 3 enables the operator to refer to the information planned before the operation in the operation. The operator can also recognize the real-time progress of the operation.

[Notification of Risk (S109)]

In an example, the processor 3 performs not only the processing and the like of S103 and S104, but also notification of risk (S109). In the operation, the processor 3 performs notification of risk based on the real-time scene recognized in S103. The processor 3 also performs notification of risk based on the real-time distance information with reference to the treatment instrument, which is generated in S104. Therefore, when performing the notification of risk of S109, the processor 3 performs the generation of real-time data of S103 and navigation of S104 in parallel. The definition of a cause of risk, which may cause risk, and that of the probability of causing risk are set in advance by pre-operation data or the like. In an example, it is set before the operation that risk may be caused when an incision is performed within a reference distance (e.g., 1 mm) from a cause of risk. The processor 3 then performs notification of a risk only when it is judged that risk may be incurred based on the real-time scene and real-time distance information with reference to the treatment instrument. In an example, the processor 3 performs notification of risk based on a result of learning using AI.

Figure 14:
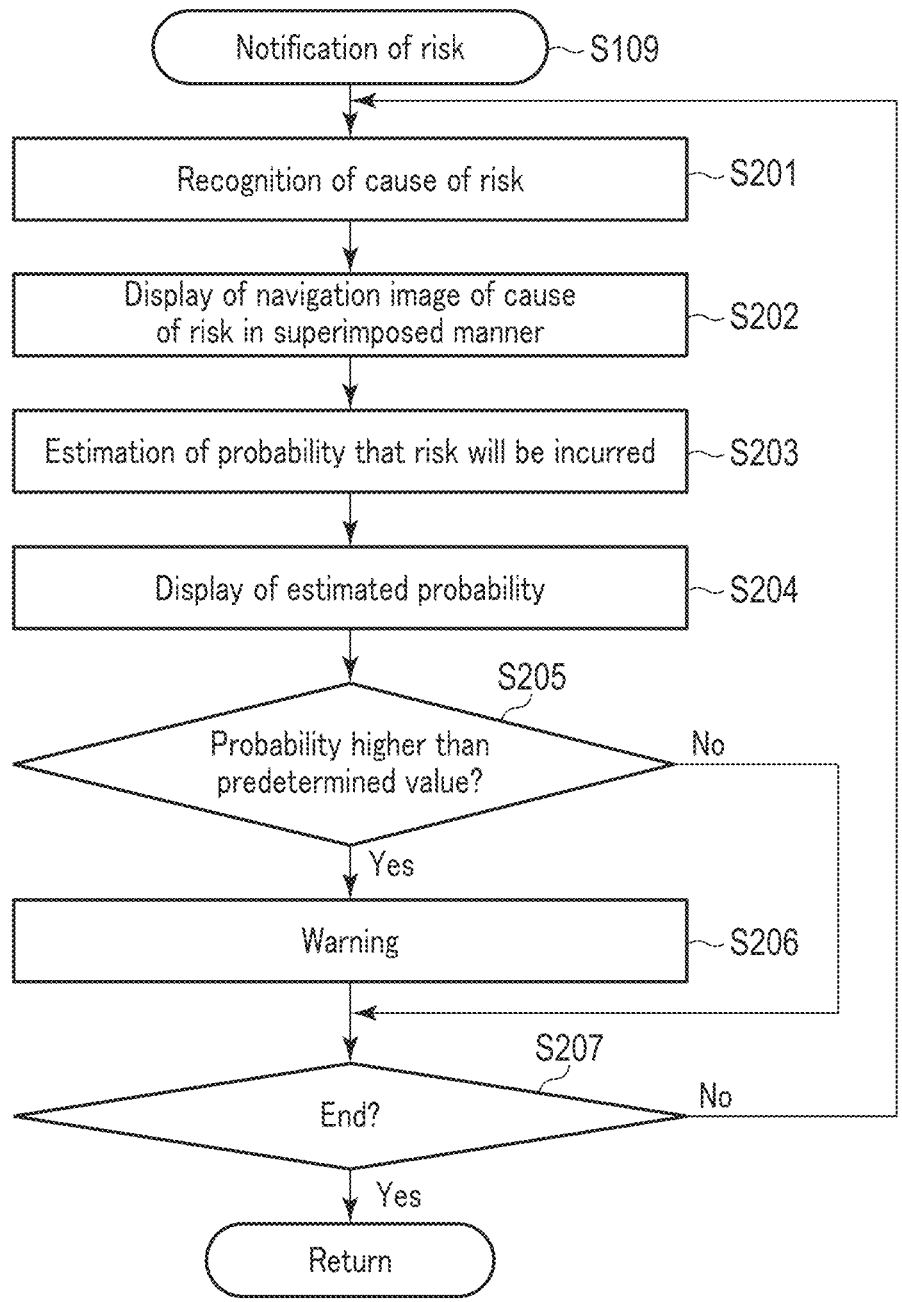
FIG. 14 is a flowchart showing processing performed in notification of risk by the processor of the operation-related information providing device according to an exemplary embodiment.

FIG. 14 shows processing performed by the processor 3 in the notification of risk. As shown in FIG. 14, the processor 3 recognizes a cause of risk, which may cause risk, in the notification of risk (S201). At this time, the processor 3 recognizes position information or the like of the cause of risk in the real-time 3D volume data generated in S103. The processor 3 also recognizes the position information of the cause of risk based on the real-time scene and real-time distance information with reference to the treatment instrument. The processor 3 then extracts the cause of risk from the real-time 3D volume data and generates a navigation image of the cause of risk. The processor 3 causes the navigation image of the cause of risk to be displayed on the endoscope image in a superimposed manner (S202).

The processor 3 then estimates the probability that risk will be incurred in real time based on the real-time scene, real-time distance information with reference to the treatment instrument, and the like (S203). The processor 3 then causes the estimated probability to be displayed together with the endoscope image (S204). The definition of the percentage or the like of the probability of causing risk is set in advance by the pre-operation data or the like. In an example, when the position of incision is at a first distance from the cause of risk, the probability of causing risk is set to 30%. When the position of incision is at a second distance from the cause of risk that is smaller than the first distance, the probability of causing risk is set to 60%. In this case, each of the first distance and the second distance is smaller than the aforementioned reference distance.

The processor 3 then judges whether or not the estimated probability is higher than a predetermined value (S205). When the estimated probability is higher than the predetermined value (Yes in S205), the processor 3 causes a warning to be issued (S206). At this time, the processor 3 may use a screen display or a lamp to visually issue a warning, or use an audio guide or a warning sound to acoustically issue a warning. Unless the processor 3 decides to terminate the processing of S109 (No in S207), the processing returns to S201. The processor 3 then sequentially performs the processing from S201 onward. Therefore, the processor 3 estimates the real-time probability that risk will be incurred as long as the processing of S109 is being performed. Accordingly, as long as the processing of S109 is being performed, i.e., the processor 3 judges that there is a possibility of causing risk, the percentage or the like of the probability of causing risk is updated.

Figure 15:
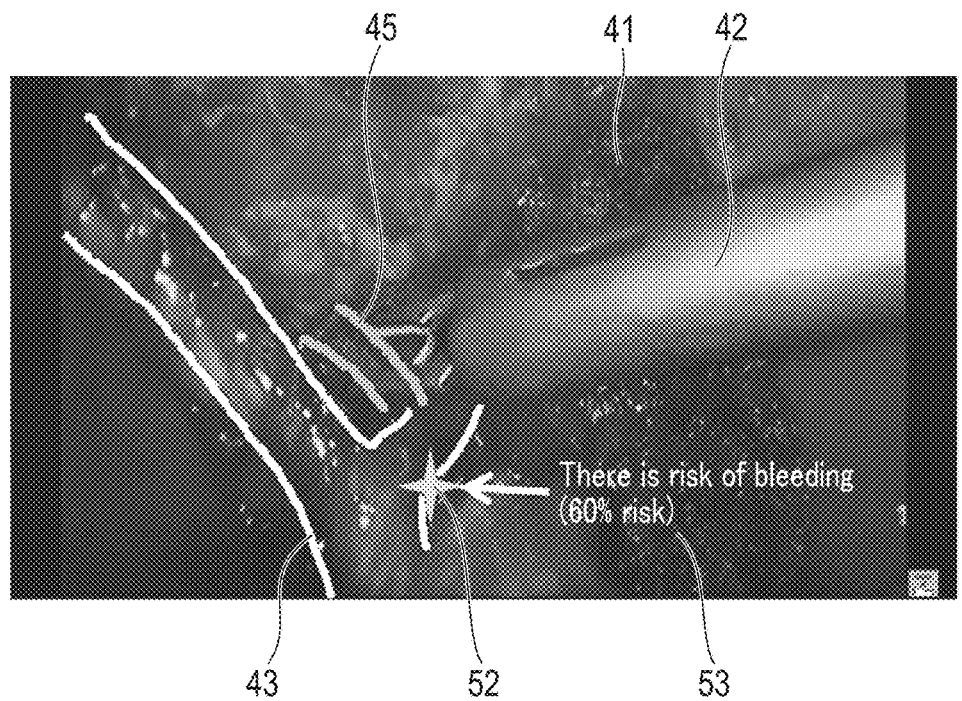
FIG. 15 is a diagram showing an example of the state where a navigation image of a cause of risk is displayed on the endoscope image in a superimposed manner in an exemplary embodiment.

In an example, the processor 3 estimates the probability of bleeding as the probability that risk will be incurred. FIG. 15 shows an example of the state where a navigation image of a cause of risk is displayed on the endoscope image in a superimposed manner. In the example of FIG. 15 also, the navigation images 43 and 45 are displayed on the endoscope image 41 in a superimposed manner. In the image of FIG. 15, a navigation image 52 of a cause of risk, which may cause bleeding, is also displayed on the endoscope image 41 in a superimposed manner. In the example of FIG. 15, the probability of bleeding from the cause of risk is estimated, and information 53 on the estimated probability is displayed.

In an example, the processor 3 estimates the probability of damaging a nerve as the probability that risk will be incurred. In the total hysterectomy surgery, the processor 3 estimates the probability of damaging the urinary system as the probability of causing risk. In intestinal perforation at an upper part of the rectum, the processor 3 estimates the probability of damaging the ureter or the like over the fat as the probability that risk will be incurred. In an example, the processor 3 recognizes a change in the temperature of an organ due to application of treatment energy from the energy device. The processor 3 then causes information on the change in the temperature of the organ to be reported.

In an example, the processor 3 recognizes a real-time anatomy status based on the endoscope image or the like. The processor 3 then estimates the risk that may be incurred in real time based on the recognized anatomy status. In an example, the processor 3 judges whether or not a surgical instrument has remained inside the body cavity after the operation. When it is recognized that a surgical instrument has remained inside the body cavity, the processor 3 causes a warning to be issued. The processor 3 also judges whether or not exfoliation is being performed in the exfoliation range determined before the operation. When it is recognized that a site different from the exfoliation range determined before the operation is exfoliated, the processor 3 causes a warning to be issued.

In an example, the processor 3 estimates the probability of interference between surgical instruments including the endoscope 13 and the treatment instrument, as well as the probability of interference between a surgical instrument and an organ, as the probability that risk will be incurred. In this case, the processor 3 estimates the probability of interference based on not only the real-time scene and the real-time distance information or the like with reference to the treatment instrument, but also the real-time positional relationship between the surgical instrument and the organ. The processor 3 also estimates the probability of interference outside the field of view of the endoscope 13, as well as the probability of interference on the endoscope image. When it is judged that the probability of interference outside the field of view of the endoscope 13 is higher than a predetermined value, the processor 3 also causes a warning to be issued.

In an example, a stapler is used as a treatment instrument in an operation, and the processor 3 judges whether or not an unintended position has been pinched by the stapler. When it is judged that an unintended portion has been pinched by the stapler, the processor 3 causes a warning to be issued. In an example, the processor 3 reports whether sufficient blood is flowing through an organ in the vicinity of the resected site. In an example, the processor 3 judges whether the patient's posture needs to be changed, based on the real-time scene. When it is judged that the posture needs to be changed, the processor causes notification to be performed. This suppresses compression by an operating table and suppresses damage to the muscle by elastic stockings in an operation to prevent venous thrombosis.

The above-described processing by the processor 3 enables the operator to recognize risk anticipated in the operation, and suppresses risk to be incurred. In addition, the processing suppresses the interference between surgical instruments and interference between a surgical instrument and an organ in the operation.

[Notification of Recommended Information (S110)]

In an example, the processor 3 performs not only the processing and the like of S103 and S104, but also notification of recommended information (S110). In the operation, the processor 3 performs notification of recommended information based on the real-time scene recognized in S103. The processor 3 also performs notification of recommended information based on the real-time distance information with reference to the treatment instrument, which is generated in S104. Therefore, when performing the notification of recommended information of S110, the processor 3 performs the generation of real-time data of S103 and navigation of S104 in parallel. In an example, the processor 3 performs notification of recommended information based on a result of learning using AI.

Figure 16:
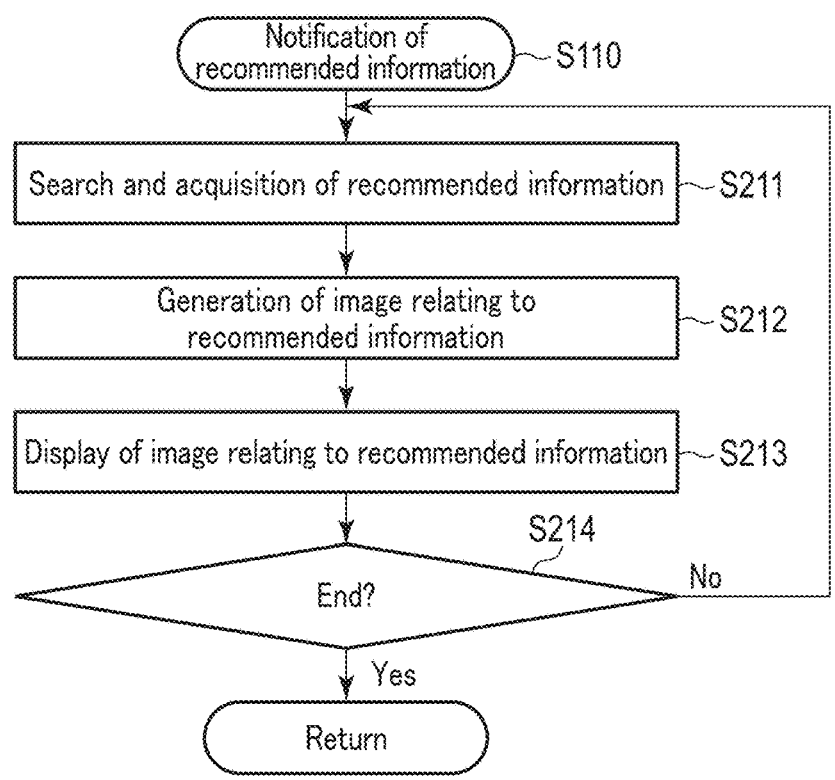
FIG. 16 is a flowchart showing processing performed in notification of recommended information by the processor of the operation-related information providing device according to an exemplary embodiment.

FIG. 16 shows processing performed by the processor 3 in the notification of recommended information. As shown in FIG. 16, in the notification of recommended information, the processor 3 searches the database 33 or the like for recommended information based on the real-time scene or the like, and acquires recommended information (S211). The processor 3 then generates an image relating to the acquired recommended information (S212). The processor 3 then causes the image relating to the recommended information to be displayed together with the endoscope image (S213). At this time, the processor 3 may display the generated image on the endoscope image in a superimposed manner.

Unless the processor 3 decides to terminate the processing of S110 (No in S214), the processing returns to S211. Then, the processor 3 sequentially performs the processing from S211 onward. Therefore, the processor 3 searches for and acquires real-time recommended information as long as the processing of S110 is being performed. Accordingly, as long as the processing of S110 is being performed, the recommended information is updated. The processor 3 causes recommended information to be reported during the period from the instruction to start the notification of recommended information to the instruction to stop the notification of recommended information. In this case, the instruction to start the notification of recommended information and the instruction to stop the notification of recommended information are each input by the operator or the like.

In an example, the processor 3 searches for and acquires treatment information in a scene similar to the real-time scene. The processor 3 then causes the treatment information in the similar scene to be displayed. In an example, the processor 3 judges which of the data in the database 33 or the like corresponds to the treatment information of the similar scene, based on a learning result using AI or the like. In an example, the operator or the like designates a scene similar to the real-time scene. The processor 3 then acquires treatment information of the similar scene designated by the operator from the database 33 or the like. In an example, the processor 3 acquires information on an accidental symptom associated with the real-time scene and causes the acquired information to be displayed. In an example, the processor 3 acquires a recommended type of treatment instrument in the real-time scene and a recommended setting value for a surgical instrument in the real-time scene, and causes the acquired information to be displayed.

In an example, the processor 3 identifies a scene corresponding to the real-time scene from data on operations performed by skilled operators. Then, the processor 3 acquires operation information or the like of a skilled operator in the identified scene, and causes the acquired information to be displayed. At this time, the processor 3 acquires a position and posture of the endoscope, an approach method, a treatment method, and the like as the operation information of the skilled operator. Further, the processor 3 acquires a type of the treatment instrument selected by the skilled operator in the identified scene and setting values for the surgical instrument used by the skilled operator in the identified scene, and causes the acquired information to be displayed.

Figure 17:
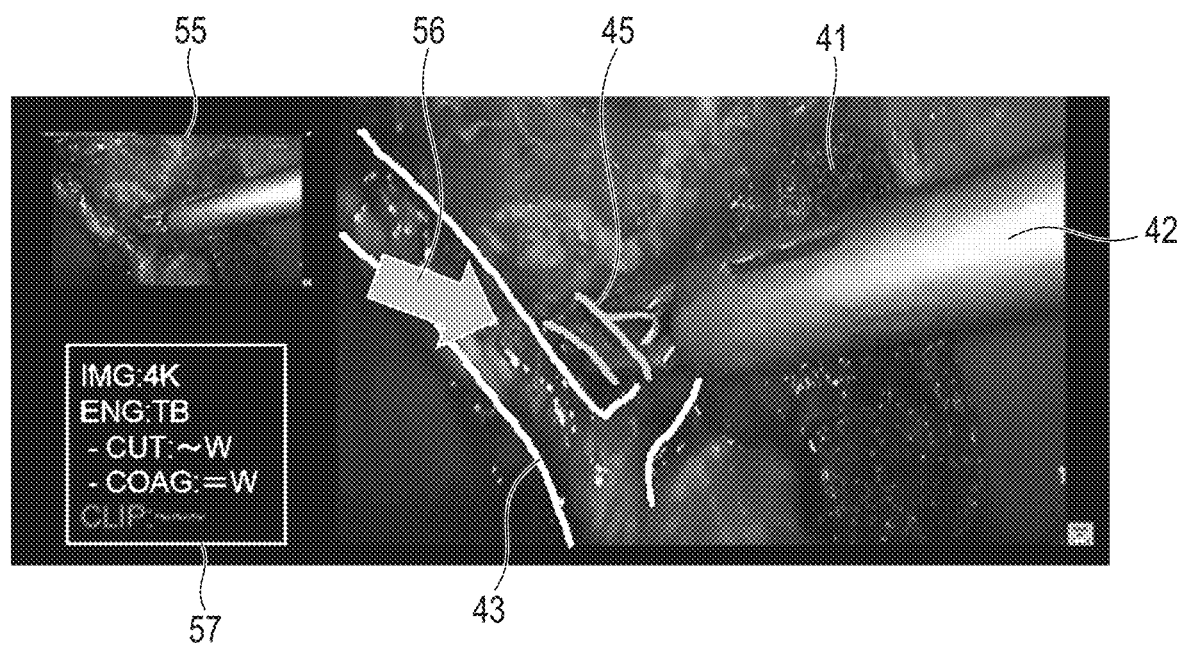
FIG. 17 is a diagram showing an example of the state where the recommendation image is displayed on the endoscope image in a superimposed manner in an exemplary embodiment.

FIG. 17 shows an example of the state where recommended information is displayed on the endoscope image in a superimposed manner. In the example of FIG. 17 also, the navigation images 43 and 45 are displayed on the endoscope image 41 in a superimposed manner. In the example of FIG. 17, the processor 3 identifies a scene in an operation performed by a skilled operator as a scene corresponding to the real-time scene. In the example of FIG. 17, an endoscope image 55 of the identified scene is displayed together with the real-time endoscope image 41. An image 56 showing the field of view of the skilled operator in the identified scene is displayed on the real-time endoscope image 41 in a superimposed manner, and information 57 indicative of a setting value relating to a surgical instrument in the identified scene is displayed together with the endoscope image 41.

In an example, the processor 3 identifies another case that can be used as a reference for the real-time scene from data in the database 33 or the like. The processor 3 then acquires information on the identified case and causes the acquired information to be displayed. In an example, the operator or the like designates another case that can be used as a reference for the real-time scene. The processor 3 then searches for and acquires information on the designated case, and causes the acquired information to be displayed. The information that the processor 3 searches the database 33 or the like for includes a moving image, a still image, a document, and the like.

The above-described processing by the processor 3 enables the operator to refer to information in a scene similar to the real-time scene in the operation. Therefore, the operator can recognize operation information of a skilled operator in the operation. Further, even if the operator is a skilled operator, the operator can refer to operation information of another operator, and can explore a new approach method, a safe approach method, or the like.

[Judgment on Re-Planning of Operation (S111)]

In an example, the processor 3 performs not only the processing and the like of S103 and S104, but also judgment on re-planning of the operation (S111). In the operation, the processor 3 performs judgment on re-planning of the operation based on the real-time 3D volume data generated in S103 and the real-time scene recognized in S103. The processor 3 also performs judgment on re-planning of the operation based on the real-time distance information with reference to the treatment instrument, which is generated in S104. Therefore, when performing the processing of S111, the processor 3 performs the generation of real-time data of S103 and navigation of S104 in parallel. The processor 3 causes the real-time state to be reflected in the real time 3D volume data generated in S103. For example, the portion pinched by a clip by the operator is reflected in the real-time 3D volume data.

Figure 18:
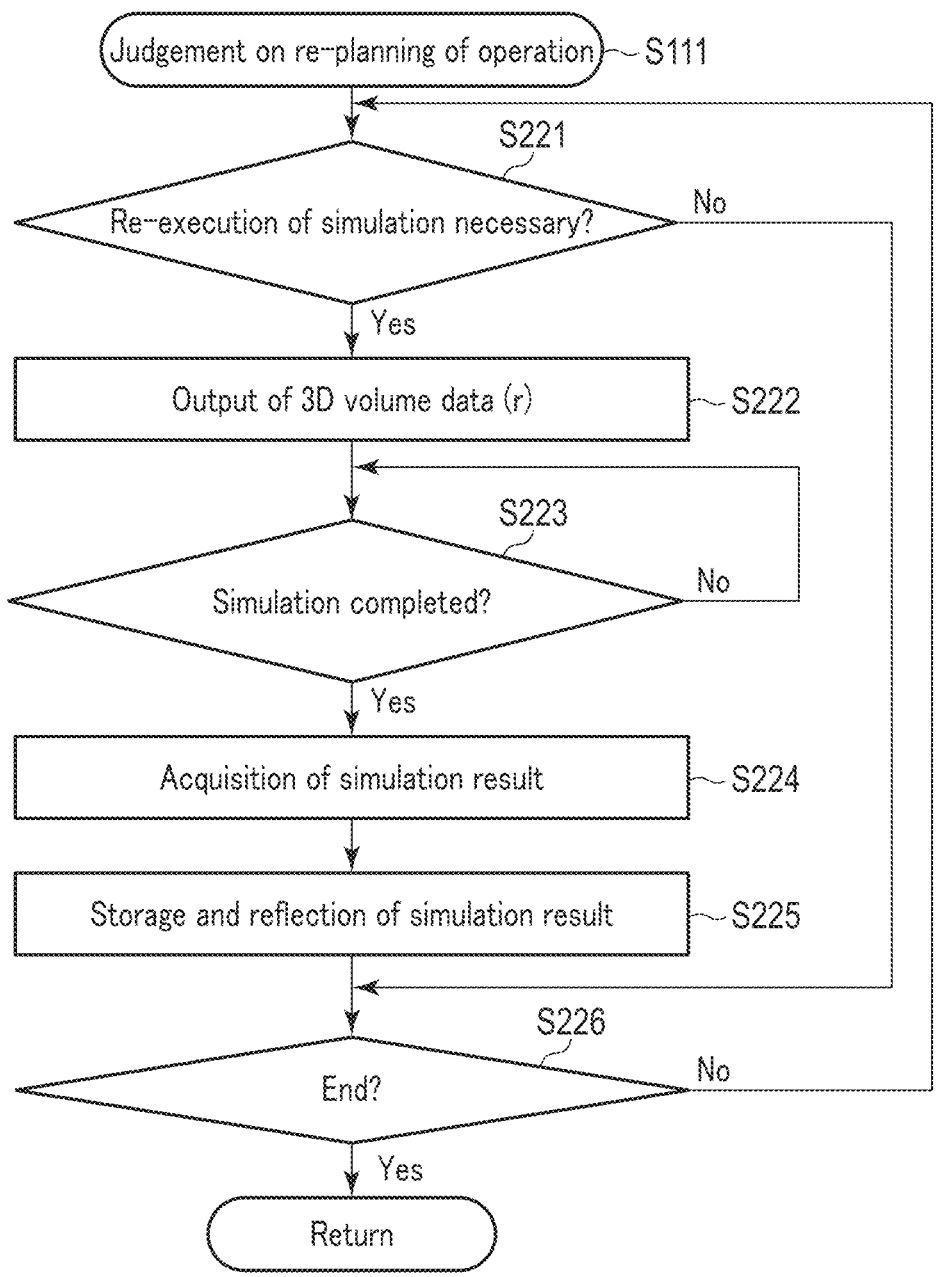
FIG. 18 is a flowchart showing processing performed in judgment on re-planning of the operation by the processor of the operation-related information providing device according to an exemplary embodiment.

FIG. 18 shows processing performed by the processor 3 in the judgment on re-planning of the operation. As shown in FIG. 18, in the judgment on re-planning of the operation, the processor 3 judges whether or not re-execution of simulation is necessary based on the real-time scene or the like (S221). At this time, the processor 3 makes a judgment as to the necessity for re-execution of simulation based not only on the real-time scene, but also on the pre-operation data such as a result of simulation performed before the operation. When it is judged that re-execution of simulation is not necessary (No in S221), the processor retains the simulation result or the like generated before the operation.

On the other hand, when it is judged that re-execution of simulation is necessary (Yes in S221), the processor 3 causes the necessity for re-execution to be reported and outputs the real-time 3D volume data to the processing device 27 (S222). The operator then re-executes the simulation on the real-time 3D volume data. At this time, the operator re-executes the simulation through the processing device 27. In the processing device 27, the simulation is re-executed based on the pre-operation data, the real-time 3D volume data, the real-time endoscope image, and the like. In the re-execution of the simulation, the operator may perform an operation on the processing device 27 or on the touch screen 7 or the like of the monitor 6. The simulation to be re-executed includes simulation of the position to be pinched by the clip, simulation to prevent anastomotic failure, simulation to prevent suture failure, and the like.

Upon completion of the re-execution of the simulation (Yes in S223), the processor 3 acquires a result of the re-executed simulation (S224). Accordingly, the processor 3 stores the result of the re-executed simulation and causes the result to be reflected in the operation plan (S225). Re-planning of the operation is thereby performed.

Unless the processor 3 decides to terminate the processing of S111 (No in S226), the processing returns to S221. The processor 3 then sequentially performs the processing from S221 onward. Therefore, the processor 3 makes a judgment as to the necessity for re-execution of the simulation in real time as long as the processing of S111 is being performed. Accordingly, as long as the processing of S111 is being performed, the operation plan is updated whenever the simulation is re-executed at the processing device 27. In an example, the operator directly edits the real-time operation plan, and the processor 3 stores the operation plan edited by the operator.

The above-described processing by the processor 3 and the processing device 27 enables the operator to confirm the appropriateness of the treatment method or the like in real time in the operation. The processing also enables the operator to change and update the operation plan in correspondence with the real-time scene or the like.

[Selection of Information to be Displayed (S112)]

In an example, the processor 3 performs not only the processing and the like of S103 and S104, but also selection of information to be displayed (S112). At this time, the processor 3 selects information to be displayed together with the endoscope image, based on the recognized real time scene, or the like. The processor 3 then generates an image for the selected information and causes the generated image to be displayed together with the endoscope image. In an example, the processor 3 selects information to be displayed together with the endoscope image, based on an instruction by the operator.

With reference to FIG. 19, the selection of information to be displayed, which is performed by the processor 3, will be described. In an example of FIG. 19, at normal times, the processor 3 causes an image to be displayed on the monitor 6 or the like as in display example A1. In display example A1, a flowchart 50 indicative of a procedure planned before the operation is displayed together with the endoscope image 41. In display example A1, the real-time task 51 is highlighted in comparison with the other tasks in the flowchart 50.

In an example of FIG. 19, in a state where risk may be incurred, the processor 3 causes an image to be displayed on the monitor 6 or the like as in display example A2. Therefore, upon change from the normal times to the state where risk may be incurred in the operation, the processor 3 switches the image to be displayed from display example A1 to display example A2. In display example A2, the navigation images 43 and 45 are displayed on the endoscope image 41 in a superimposed manner. In display example A2, the navigation image 52 of a cause of risk, which may cause bleeding, is also displayed on the endoscope image 41 in a superimposed manner. In display example A2, the probability of bleeding from the cause of risk is estimated, and information 53 on the estimated probability is displayed. In display example A2, an image 48 relating to vital information is displayed together with the endoscope image 41.

In an example of FIG. 19, in the state where the operation is being re-planned, the processor 3 causes an image to be displayed on the monitor 6 or the like as in display example A3. Therefore, upon change from the normal times to the state where the operation is being re-planned, the processor 3 switches the image to be displayed from display example A1 to display example A3. In display example A3, a result 47 of simulation performed before the operation is displayed on the endoscope image 41 in a superimposed manner.

By the processor 3 performing processing as described above, appropriate information corresponding to the real-time scene is displayed together with the endoscope image. In addition, information required by the operator in real time is displayed together with the endoscope image.

(Modification)

In a modification, the operation-related information providing device 2 is integrated with one or more of the view controlling device 21, the image processor 17, the processing device 27, and the like to form one operation-related information providing device. In this case, the operation supporting device includes one or more processors. The processor of the operation supporting device performs not only the above-described processing performed by the processor 3 of the operation-related information providing device 2, but also the processing of the device(s) integrated with the operation-related information providing device 2 among the view controlling device 21, the image processor 17, the processing device 27, and the like.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation supporting device comprising a processor configured to:
  acquire pre-operation data, the pre-operation data including position information of a feature portion from an inside of a body of a subject, is the position information being generated before an operation;
  acquire a planned procedure in the operation that includes creation and simulation of an operation plan before the operation;
  acquire an endoscope image generated in the operation;
  generate real-time data including real-time position information of the feature portion based at least on the pre-operation data and the endoscope image;
  generate an image to superimpose on the endoscope image based on the real-time data; and
  recognize a real-time scene based at least on the planned procedure and the real-time data.

2. The operation supporting device according to claim 1, wherein the processor is configured to:
  acquire, as the pre-operation data, 3D volume data generated from information on the subject before the operation; and
  recognize the feature portion in the 3D volume data and thereby configured to acquire the position information of the feature portion.

3. The operation supporting device according to claim 2, wherein
  the processor is configured to generate real-time space information about an inside of the body based on the endoscope image, and
  based on the endoscope image and the real-time space information, the processor is configured to:
    convert the 3D volume data acquired as the pre-operation data, and
    generate real-time 3D volume data including the real-time position information of the feature portion.

4. The operation supporting device according to claim 1, wherein
  the processor is configured to acquire, as the pre-operation data, the planned procedure and an estimated required time for each of a plurality of tasks of the planned procedure.

5. The operation supporting device according to claim 1, wherein the processor is configured to:
  recognize a bleeding position when bleeding occurs in the endoscope image, and
  generate a navigation image relating to the recognized bleeding position to superimpose on the endoscope image.

6. The operation supporting device according to claim 1, wherein:
the processor is configured to acquire information sensed, measured, or observed by a device disposed outside the body in the operation, and
the processor is configured to recognize the real-time scene based on the planned procedure and the real-time data and the information sensed, measured, or observed by the device disposed outside the body.

7. The operation supporting device according to claim 6, wherein:
the processor is configured to acquire, as the information sensed, measured, or observed by the device disposed outside the body, a position of a port through which a surgical instrument including an endoscope and a treatment instrument is inserted, a type of surgical instrument inserted from the port, and information about an operator of the operation.

8. The operation supporting device according to claim 1, wherein:
the processor is configured to recognize a real-time task from among a plurality of tasks of the planned procedure based on the recognized real-time scene, and
the processor is configured to display the planned procedure with the endoscope image such that the recognized real-time task is highlighted in the displayed procedure.

9. The operation supporting device according to claim 1, wherein:
the processor is configured to select and generate information to be displayed together with the endoscope image, based on the recognized real-time scene.

10. The operation supporting device according to claim 1, wherein:
The processor is configured to estimate a probability that risk will be incurred in real time, based on the recognized real-time scene, and
the processor is configured to issue a warning when an estimated probability is higher than a predetermined value.

11. The operation supporting device according to claim 10, wherein:
the processor is configured to estimate the probability that risk will be incurred by determining
a probability of causing bleeding or damage to a nerve,
a probability of interference between surgical instruments including an endoscope and a treatment instrument, and
a probability of interference of the surgical instruments with an organ.

12. The operation supporting device according to claim 1, wherein:
the processor is configured to cause recommended information relating to treatment in the recognized real-time scene to be displayed together with the endoscope image, based on the recognized real-time scene.

13. The operation supporting device according to claim 12, wherein:
the processor is configured to cause one or more of the following to be displayed as the recommended information relating to the treatment in the recognized scene: (1) treatment information in a scene similar to the recognized real-time scene, (2) information on an accidental symptom relating to the recognized real-time scene, (3) a type of a treatment instrument recommended in the recognized real-time scene, and (4) recommended setting values for surgical instruments including an endoscope and the treatment instrument in the recognized real-time scene.

14. The operation supporting device according to claim 1, wherein:
the processor is configured to acquire, as the pre-operation data: (1) 3D volume data generated from information on the subject before the operation, and (2) a result of a simulation of the operation performed before the operation.

15. The operation supporting device according to claim 14, wherein:
the processor is configured to make a judgment as to a necessity for re-execution of the simulation of the operation, based on the recognized real-time scene and the result of the simulation of the operation acquired as the pre-operation data.

16. The operation supporting device according to claim 15, wherein:
the processor is configured to generate real-time 3D volume data including the real-time position information of the feature portion, based at least on the pre-operation data and the endoscope image, and
when it is judged to re-execute the simulation of the operation, the processor is configured to re-execute simulation of the operation in the real-time 3D volume data, and configured to acquire a result of the re-executed simulation of the operation.

17. The operation supporting device according to claim 1, wherein the processor is configured to:
acquire diagnostic information and patient information before the operation;
generate 3D volume data of an inside of the body of the subject based at least on the diagnostic information and the patient information;
set the position information of the feature portion in the generated 3D volume data;
perform simulation of the operation in the generated 3D volume data; and
create the planned procedure based on a result of the simulation.

18. The operation supporting device according to claim 17, wherein
the processor is configured to:
acquire an operation plan including the planned procedure based on the result of the simulation,
recognize the feature portion on the acquired endoscope image,
generate real-time 3D volume data of an inside of the body of the subject based at least on the acquired endoscope image and the 3D volume data generated before the operation, and
recognize the real-time scene based at least on the real-time 3D volume data and the operation plan.

19. A method of operating an operation supporting device, the method comprising:
acquiring a planned procedure in an operation that includes creation and simulation of an operation plan before the operation;
acquiring an endoscope image generated in the operation;
recognizing a feature portion of a subject on the acquired endoscope image;
generating real-time 3D volume data of an inside of a body of the subject including the feature portion, based on the acquired endoscope image; and
recognizing a real-time scene based at least on the real-time 3D volume data and the planned procedure.

20. The operation supporting according to claim 1, wherein the feature portion includes at least one of the following: a vessel blood vessel, a lymph vessel, an organ, a nerve, a tumor, or a lymph node.

* * * * *